United States Patent [19]

Reed et al.

[11] Patent Number: 5,702,897
[45] Date of Patent: Dec. 30, 1997

[54] INTERACTION OF PROTEINS INVOLVED IN A CELL DEATH PATHWAY

[75] Inventors: John C. Reed, Carlsbad; Takaaki Sato, San Diego, both of Calif.

[73] Assignee: The Burnham Institute, La Jolla, Calif.

[21] Appl. No.: 607,269

[22] Filed: Feb. 20, 1996

Related U.S. Application Data

[63] Continuation of Ser. No. 226,876, Apr. 13, 1994, abandoned.
[51] Int. Cl.$^6$ ............................................. C12Q 1/68
[52] U.S. Cl. ............................. 435/6; 435/29; 435/69.1
[58] Field of Search ........................... 435/6, 29, 69.1

[56] References Cited

PUBLICATIONS

Fernandez–Sarabia et al., *Nature*, vol. 366, 18 Nov. 1993, pp. 274–275.
Fields et al., *Nature*, vol. 340, 1989, pp. 245–246.
Cotter et al., *Anticancer Research*, vol. 12, 1992, pp. 773–780.
Fearon et al., *PNAS*, vol. 89, 1992, pp. 7958–7962.
Boise et al., *Cell*, vol. 74, 27 Aug. 1993, pp. 597–608.
Oltvai et al., *Cell*, vol. 74, 27 Aug. 1993, pp. 609–619.
Bright et al., *Bioscience Reports*, vol. 14, 1994, pp. 67–81.

*Primary Examiner*—James Ketter
*Attorney, Agent, or Firm*—Campbell & Flores LLP

[57] ABSTRACT

The present invention provides methods for detecting an interaction among proteins involved in regulating cell death. The invention also provides a drug screening assay useful for identifying agents that alter an interaction among proteins involved in controlling cell death. The invention further provides a method for identifying novel proteins that are involved in a cell death pathway.

5 Claims, 6 Drawing Sheets

```
HUMAN BCL-2     M------------- -------------- -------------- ----------AH AG--------R TGYDNREI-- -----VM---       16
RAT BCL-2       M------------- -------------- -------------- ----------AQ AG--------R TGYDNREI-- -----VM---       16
MOUSE BCL-2     M------------- -------------- -------------- ----------AQ AG--------R TGYDNREI-- -----VM---       16
CHICKEN BCL-2'  M------------- -------------- -------------- ----------AH PG--------R RGYDNREI-- -----VL---       16
BCL-X           M------------- -------------- -------------- ----------SQ S---------- --NREL---- -----VV---       10
BAX             M------------- -------------- -------------- ----------DG SG-------- --------E- ----------        6
MCL-1           MFGLKRNAVI GLNLYCGGAG LGAGSGGATR PGGRLLATEK EASARRRIGG GEAGAVIGGS                                  75
LMW5-HL         M------------- -------------- -------------- ----------   -G-------- ----------  ----------       3
BHRF1           M------------- -------------- -------------- ----------AY ST-------- --REI----- -----LL---      10
Consensus       M............. .............. .............. ..........A. .G........ ...NREI... .....V....      75

HUMAN BCL-2     -------------- -------------- ----------K YIHYKLSQRG YEWDAGDVGA APPGAAPA-- -------------- ---QP     53
RAT BCL-2       -------------- -------------- ----------K YIHYKLSQRG YEWDTGDEDS APLRAAPT-- -------------- ---QP     53
MOUSE BCL-2     -------------- -------------- ----------K YIHYKLSQRG YEWDAGDADA APLGAAPT-- -------------- ---QP     53
CHICKEN BCL-2'  -------------- -------------- ----------K YIHYKLSQRG YDWAAGE-DR PPVPPAPA-- -------------- ---AV     52
BCL-X           -------------- -------------- ----------D FLSYKLSQKG YSWSQFSDVE ENRTEAPE-- -------------- ---ET     47
BAX             -------------- -------------- ----------   -QPRG ---GGPTSS EQIMKT---- ----------   ---Q--      28
MCL-1           VARPPPIGAE VPDVTATPAR LLFFAPTRRA APLEEMEAPA ADAIMSPEEE LDGYEPEPLG KRPAVLPLLE LVGES             150
LMW5-HL         -------------- -------------- ----------   -EELI Y-----HNII NEILV----- ----------   -GYIKY-      22
BHRF1           -------------- -------------- ----------   -ALCIRD ---SRVHG NGTLH----- ----------   -PVLEL-      31
Consensus       .............. .............. ..........   YKLSQRG Y.W.G..... ......AP.. .............. ...PG..    150
```

FIG. 5A

```
HUMAN BCL-2     GHTPHTAASR DPVARTS--- ---------- -------PLQ TP---AAPGA AAGPALSPV- -----PPVVHL -TLRQAGDDF SRRYR    109
RAT BCL-2       ESNRTPAVHR DTAARTS--- ---------- -------PLR -P---LV--A NAGPALSPV- -----PPVVHL -TLRRAGDDF SRRYR    106
MOUSE BCL-2     ESNPMPAVHR EMAARTS--- ---------- -------PLR -P---LV--A TAGPALSPV- -----PPCVHL -TLRRAGDDF SRRYR    106
CHICKEN BCL-2   AAAGASSHHR -PEPPGS--- ---------- -------AAA -S----EV-- PPAEGLRPA- -----PPGVHL -ALRQAGDEF SRRYQ    103
BCL-X           PSAINGNPSW HLADSPA--- ---------- -------VNG AT---AHSSS LDAREVIPM- -----AAVKQ- -ALREAGDEF ELRYR    102
BAX             GFIQDRAGRM GGEAPEL--- ---------- -------ALD -P---V---- PQDASTKKL- -----SEC--- -LKRIGDEL DS--N     73
MCL-1           GNNTSTDGSL PSTPPPAEEE EDELYRQSLE IISRYLREQA TGAKDTKPMG RSGATSRKAL ETLRRVGDGV QRNHE              225
LMW5-HL         -YMNDISEH- ---------- ---------- -------ELS ---------- PYQQIKKI-- ---------- -LTYYDECL NKQVT     55
BHRF1           -AARETPLRL SPEDTV---- ---------- -------VLR ---------- -YHVLLEEI- ---------- -IERNSETF TETWN     70
Consensus       .......... .......... .......... ........L. .......... ....L.P.-. ---------- -.LRRAGD.F .RRY.    225

HUMAN BCL-2     RDFAEMSRQL HLTPFTARGR FATVVEELFR DG-VNWGRIV AFFEFGGVMC VESVNREMSP -LVDNIALWM TEYLN               182
RAT BCL-2       RDFAEMSSQL HLTPFTARGR FATVVEELFR DG-VNWGRIV AFFEFGGVMC VGSVNREMSP -LVDNIALWM TEYLN               179
MOUSE BCL-2     RDFAEMSSQL HLTPFTARGR FATVVEELFR DG-VNWGRIV AFFEFGGVMC VESVNREMSP -LVDNIALWM TEYLN               179
CHICKEN BCL-2   RDFAQMSGQL HLTPFTAHGR FAVVVEELFR DG-VNWGRIV AFFEFGGVMC VESVNREMSP -LVDNIATWM TEYLN               176
BCL-X           RAFSDLTSQL HITPGTAYQS FEQVVNELFR DG-VNWGRIV AFFSFGGALC VESVDKEMQV -LVSRIAAWM ATYLN               175
BAX             MELQRMIAAV DTD--SPREV FFRVAADMFS DGNFNWGRVV ALFYFASKLV LKALCTKVPE -LIRTIMGWT LDFLR               145
MCL-1           TVFQGMLRKL DIKNEDDVKS LSRVMIHVFS DGVTNWGRIV TLISFGAFVA KHLKTINQES -CIEPLAESI TDVLV               299
LMW5-HL         ITFS-LINAQ EI-----KTQ FTGVVTELFK DL-INWGRIC GFIVFSARM- AKYCKDANNH -LESTVITTA YNFMK               121
BHRF1           R-FITHTEHV DL-------D FNSVFLEIFH RGDPSLGRAL AWMAWCMHAC RTLCCNQSTP YVVVDLSVRG MLEAS               137
Consensus       R.F.M..QL HLTP.TA... F..VV.ELFR DG-VNWGRIV AFF.FGG.MC V.SV..EM.P -LV..IA.WM T.YLN                300
```

FIG. 5B

| | | | | | |
|---|---|---|---|---|---|
| HUMAN BCL-2 | RHLHTWIQDN | GGWDAFVELY | GPSMRPLFDF | SWLSLKT-LL | SLALVGACIT | LGAYLGHK | 239 |
| RAT BCL-2 | RHLHTWIQDN | GGWDAFVELY | GPSMRPLFDF | SWLSLKT-LL | SLALVGACIT | LGAYLGHK | 236 |
| MOUSE BCL-2 | RHLHTWIQDN | GGWDAFVELY | GPSMRPLFDF | SWLSLKT-LL | SLALVGACIT | LGAYLGHK | 236 |
| CHICKEN BCL-2 | RHLHNWIQDN | GGWDAFVELY | GNSMRPLFDF | SWISLKT-IL | SLVLVGACIT | LGAYLGHK | 233 |
| BCL-X | DHLEPWIQEN | GGWDTFVELY | GNNAAAESRK | GQERFNRWFL | TGMTVAGVVL | LGSLFSRK | 233 |
| BAX | ERLLGWIQDQ | GGWDGLLSYF | GTP------- | TWQTVT---IF | VAGVLTASLT | IWKKMG-- | 192 |
| MCL-1 | RTKRDWLVKQ | RGWDGFVEFF | HVE-----DL | E-GGIRNVLL | AFAGVAGVGA | GLAYLIR- | 350 |
| LMW5-HL | HNLLPWMMISH | GGQEEFLAFS | LHSDIYSVIF | NIKYFLSKFC | NHMFLRSCVQ | LLRNCNLI | 179 |
| BHRF1 | EGLDGWIHQQ | GGWSTLIEDN | IPGSR---RF | SWTLFLA-GL | TLSLLVICSY | LFISRGRH | 191 |
| | | | | | | | 358 |
| Consensus | RHL..WIQDN | GGWD.FVELY | G.S.R...DF | SW.......L | .L..V.AC.T | LGAYLG.K |

FIG. 5C

INTERACTION OF PROTEINS INVOLVED IN A CELL DEATH PATHWAY

This application is a continuation of application Ser. No. 08/226,876, filed Apr. 13, 1994, now abandoned.

This work was supported by grant number CA 60181 awarded by the National Cancer Institute. The United States Government has certain rights in this invention.

BACKGROUND OF THE INVENTION

FIELD OF THE INVENTION

This invention relates generally to the fields of cellular biochemistry and cell death and more specifically to the interaction of proteins involved in cell death.

BACKGROUND INFORMATION

Programmed cell death is a physiologic process that ensures homeostasis is maintained in essentially all self-renewing tissues between cell production and cell turnover. In many cases, characteristic morphological changes, termed "apoptosis," occur in a dying cell. Since similar changes occur in different types of dying cells, cell death appears to proceed through a colon pathway in different cell types.

In addition to maintaining tissue homeostasis, apoptosis also occurs in response to a variety of external stimuli, including growth factor deprivation, alterations in $Ca^{2+}$ levels, free-radicals, cytotoxic lymphokines, infection by some viruses, radiation and most chemotherapeutic agents. Thus, apoptosis is an inducible event that is likely subject to similar mechanisms of regulation as occur, for example, in a metabolic pathway. In this regard, dysregulation of apoptosis also can occur and is observed, for example, in some types of cancer cells, which survive for a longer time than corresponding normal cells, and in neurodegenerative diseases where neurons die prematurely.

Some of the proteins involved in programmed cell death have been identified and some interactions among these proteins have been described. However, the mechanisms by which these proteins mediate their activity remains unknown. It is likely that other as yet unidentified proteins also are involved in a cell death pathway. The identification of the proteins involved in cell death and an understanding of the interactions between these proteins can provide a means for manipulating the process of apoptosis in a cell and, therefore, selectively regulating the relative lifespan of a cell.

Thus, a need exists to identify novel proteins involved in a cell death pathway, to manipulate the interactions among these proteins and to obtain agents that can effectively alter these interactions and, thereby, alter the level of apoptosis in a cell. The present invention satisfies this need and provides additional advantages as well.

SUMMARY OF THE INVENTION

The present invention provides a screening assay useful for identifying an effective agent, which can alter the interaction among proteins involved in regulating cell death. Such effective agents are useful for increasing or decreasing the level of apoptosis in a cell.

The invention further provides a method for identifying novel proteins that are involved in a cell death pathway. Such proteins can act as upstream activators or downstream effectors of a cellular protein such as Bax, which induces apoptosis in a cell. Such proteins also can be members of the Bcl-2 protein family, which can decrease the level of apoptosis in a cell by binding to Bax.

LexA fusion proteins were produced by inserting a cDNA encoding an open reading frame of a protein such as Bcl-2 or a Bcl-2-related protein into one of the restriction sites indicated in the polylinker, which is downstream of the nucleic acid sequence encoding LexA (Lex202). Cloning was performed so as to maintain the open reading frame of LexA into the inserted sequence such that a LexA fusion protein is produced. If necessary, PCR was used to introduce an Eco RI site into the cDNA, while maintaining the proper reading frame. The nucleic acid encoding the fusion protein was expressed from an alcohol dehydrogenase promotor (ADHpro).

Figure 2:
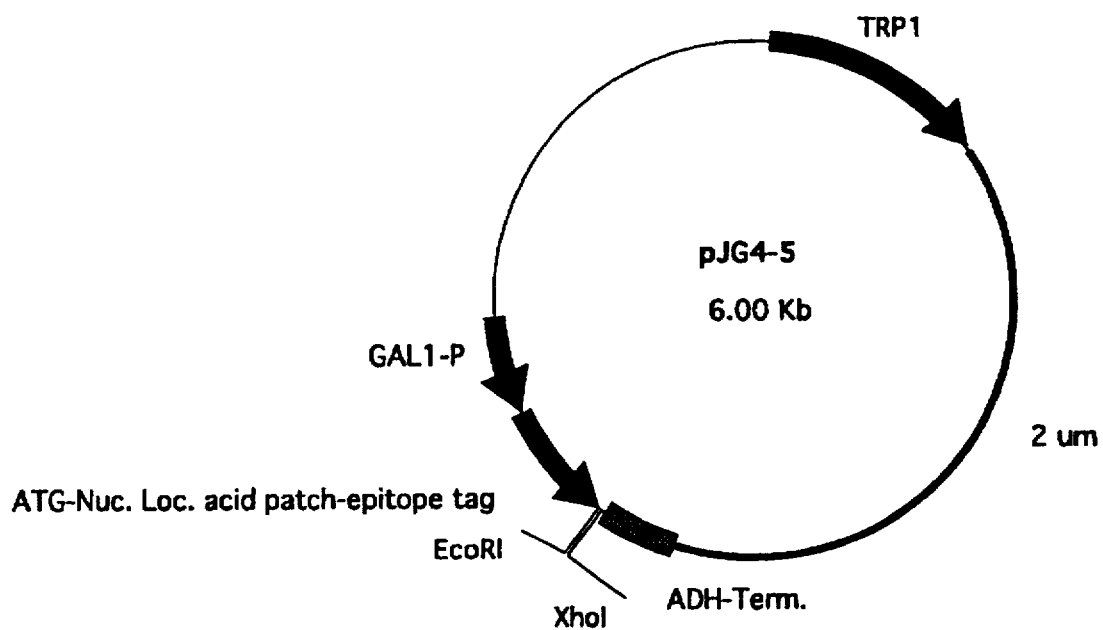

FIG. 2 provides a map of plasmid pJG4-5, which was used to produce B42 fusion proteins. The plasmid contains a 2 micron (2 μm) yeast origin of replication and a gene that allows a yeast cell containing the plasmid to grow in medium lacking tryptophan (TRP1).

A B42 fusion protein is produced by inserting a nucleic acid encoding a protein such as Bcl-2 or a Bcl-2-related protein into the Eco RI or Xho I sites located downstream of a cassette encoding an initiator methionine (ATG), an SV40 nuclear localization signal (Nuc. Loc.), B42 trans-activator (acid patch) and a hemagglutinin HA1 epitope tag. The nucleic acid encoding the B42 fusion protein is expressed from a galactose-inducible promotor (GAL1-p).

Figure 3:
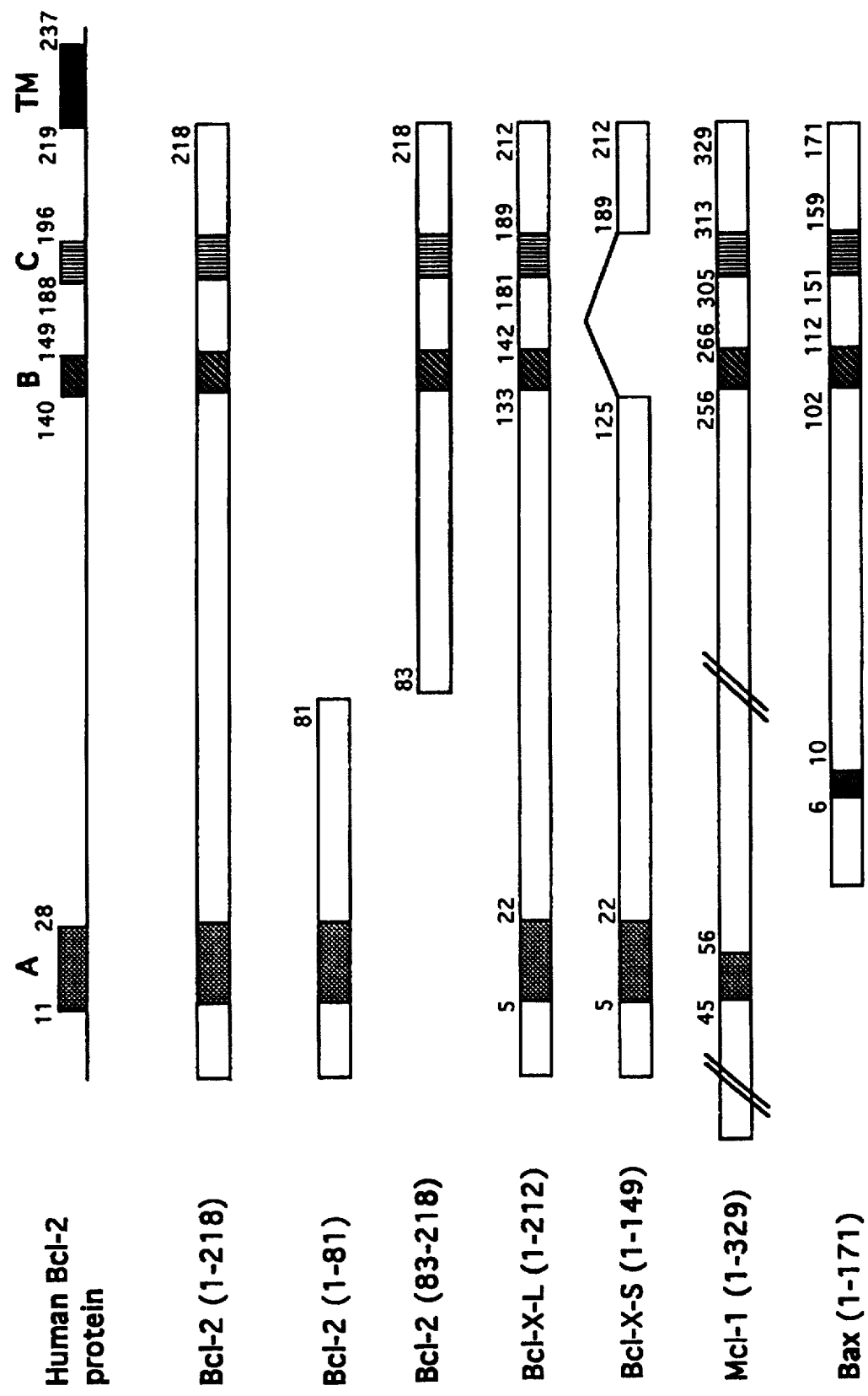

FIG. 3 illustrates the structures of various Bcl-2 and Bcl-2-related proteins. Numbers indicate amino acid residues. The complete human Bcl-2 protein structure is shown for comparison. The transmembrane region (TM), which was deleted in each of the constructs, and the highly conserved regions (A, B and C) are indicated (see FIG. 5; Sato et al., Gene 140:291–292 (1994)). In the Bcl-X-S(1-149) structure, the line indicates the region that deleted in this protein as a result of alternative RNA splicing.

Figure 4:
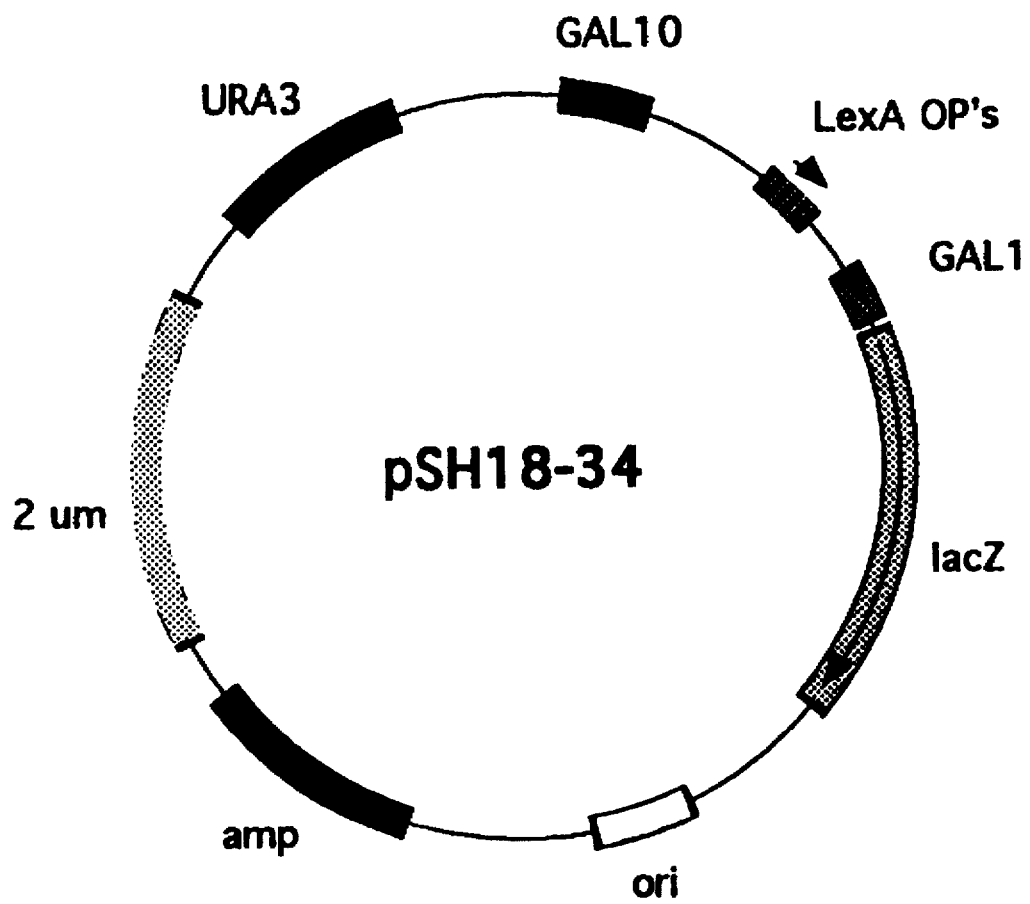

FIG. 4 provides a map of plasmid pSH18-34, which contains the reporter lacZ gene encoding β-galactosidase. The plasmid contains a bacterial origin of replication (ori) and an ampicillin resistance gene (amp). The plasmid also contains a yeast 2 micron (2 μm) origin of replication and a gene that allows a yeast cell containing the plasmid to grow in the absence of uracil (URA3). The lacZ gene is linked to a galactose-inducible promotor (GAL1). In addition to galactose, expression of the lacZ gene depends on LexAbinding to the Lex operator sequences (Lex A Op's) and trans-activation. pSH18-34 contains 8 LexA operators (LexA binding sites).

FIG. 5 shows the amino acid sequences for various members of the Bcl-2 protein family (SEQ ID NOS.20-29). Numbers in the right hand column indicate the amino acid numbers.

DETAILED DESCRIPTION OF THE INVENTION

The present invention provides methods for detecting an interaction among proteins involved in the regulation of cell death. Proteins such as Bcl-2 and Bcl-2-related proteins can modulate apoptosis in a cell. For example, Bcl-2 can prevent or delay apoptosis in a cell and likely regulates a common final pathway that leads to apoptotic cell death. Alterations in Bcl-2 levels and abnormal patterns of Bcl-2 expression occur in adenocarcinoma of the prostate, squamous cell cancer of the lung, nasopharyngeal carcinomas and neuroblastomas. These observations as well as gene transfer experiments and the use of transgenic mice indicate that Bcl-2 expression can contribute to the pathogenesis of human cancer by blocking programmed cell death (apoptosis) and, thereby, allowing expansion of the cancer cell population.

The deduced amino acid sequence of the 26 kiloDalton (kDa) human Bcl-2 (SEQ ID NO.20) protein has no significant homology with any protein having a known biochemical activity. However, Bcl-2 can interact with a small molecular weight GTPase member of the ras family, p23-R-Ras, which can bind the serine/threonine protein kinase, Raf-1. Thus, Bcl-2 may regulate a signal transduction pathway involving R-Ras and Raf-1.

Bcl-2 can form heterodimers with a 21 kDa Bcl-2-related protein, Bax (SEQ ID NO.25; Oltvai et al, Cell 74:609–619 (1993)). The Bax-α protein, which is a membrane-bound form of Bax, has approximately 21% identity and 43% similarity with Bcl-2. Bax and Bcl-2 also share various topological features, including, for example, a hydrophobic stretch of amino acids near their C-termini. In Bcl-2, this hydrophobic tail constitutes a transmembrane domain that is necessary for targeting Bcl-2 to specific intracellular locations. This hydrophobic region also is required for optimal Bcl-2 activity in blocking cell death.

Bcl-2 expression can prolong survival of lymphokine-dependent hemopoietic cells in culture following transfer of the cells to lymphokine-deficient medium. Bax expression abrogates the ability of Bcl-2 to prolong cell survival in response to growth factor withdrawal. It is unclear, however, whether Bcl-2 induces a pathway that actively maintains cell survival, with Bax serving as a negative regulator of Bcl-2 activity, or whether Bax generates a signal for cell death, with Bcl-2 acting as a dominant inhibitor of Bax activity.

In addition to the bax gene, other cellular genes encode Bcl-2-related proteins, which share sequence homology with Bcl-2 (see FIG. 3). The bcl-X gene, for example, can generate two proteins via alternative splicing (SEQ ID NO.24; Boise et al., Cell 74:597–608 (1993), which is incorporated herein by reference). One form of the alternatively spliced bcl-X transcript encodes Bcl-X-L (long form), which is a 241 amino acid protein that has 44% sequence identity with Bcl-2. Expression of Bcl-X-L, like Bcl-2, can suppress cell death. The other alternatively spliced form of bcl-X, Bcl-X-S (short form), encodes a 178 amino acid protein that is missing amino acids 126 to 188 as found in Bcl-X-L (Boise et al., supra, 1993). Bcl-X-S functions as a dominant inhibitor of Bcl-2 activity. However, unlike Bax, Bcl-X-S was not observed to bind Bcl-2 to form heterodimers in vitro (Boise et al., supra, 1993).

The family of Bcl-2-related proteins also include Mcl-1 (SEQ ID NO.26) and A1, which share approximately 35% and 40% sequence identity, respectively, over a 80 to 139 amino acid region present in the p26 human Bcl-2 protein. As used herein, the term "Bcl-2-related" protein refers to a protein that is structurally related to Bcl-2 (see FIG. 3). Bcl-X-L, Bcl-X-S and Mcl-1, for example, are structurally related to Bcl-2 and, in addition, can physically interact with Bcl-2, with Bax and with each other. Thus, Bcl-2-related proteins are characterized, not only by the structural similarities shared between these proteins, but also, as disclosed herein, by their ability to interact with Bcl-2 and with each other.

In addition, the term "Bcl-2 protein family" is used to encompass Bcl-2 and Bcl-2-related proteins and active fragments of these proteins. The term "protein" is used in its broadest sense to mean a sequence of amino acids that is encoded by a cellular gene or by a recombinant nucleic acid sequence. A protein can be the complete, full length gene product or an active fragment thereof. A protein also can be a post-translationally modified form of a protein such as a phosphoprotein, glycoprotein, proteoglycan, lipoprotein and nucleoprotein. Examples of the Bcl-2 protein family include Bcl-2 and the Bcl-2-related proteins, Bax, Bcl-X-L, Bcl-X-S, Mcl-1 and A1, as well as active fragments of these proteins. As used herein, the term "active fragment" means a portion of a full length protein of the Bcl-2 protein family that can function, at least in part, like a member of the Bcl-2 protein family. For example, Bcl-2(1-81) and Bcl-2(83-218) are active fragments of Bcl-2 that can form "homodimers" with Bcl-2 and can form heterodimers with various Bcl-2-related proteins. Active fragments can be identified using the two-hybrid assay described below or can be identified by affecting Bax-induced death of yeast/mBax cells (see Example III). The structural similarities and functional interactions of these proteins with each other indicate that the members of the Bcl-2 protein family regulate apoptosis in a cell.

As used herein, the term "interaction" or "interact" means that two or more proteins can bind to each other relatively specifically. A protein-protein interaction can be detected using a variety of methods, including, for example, measuring the ability of the proteins to bind each other in vitro or using a transcription activation assay such as the two-hybrid assay described below. A protein-protein interaction assay provides a means for screening agents that potentially can alter the interaction of proteins involved in regulating cell death and allows the identification of effective agents that alter such interactions.

A transcription activation assay such as the yeast two-hybrid system allows for the identification and manipulation of protein-protein interactions (Fields and Song, Nature 340:245–246 (1989), which is incorporated herein by reference). The conceptual basis for a transcription activation assay is predicated on the modular nature of transcription factors, which consist of functionally separable DNA-binding and trans-activation domains. When expressed as separate proteins, these two domains fail to mediate gene transcription. However, the ability to activate transcription can be restored if the DNA-binding domain and the trans-activation domain are bridged together through a protein-protein interaction. These domains can be bridged, for example, by expressing the DNA-binding domain and trans-activation domain as fusion proteins (hybrids), where the proteins that are appended to these domains can interact with each other. The protein-protein interaction of the hybrids can bring the DNA-binding and trans-activation domains together to create a transcriptionally competent complex.

One adaptation of the transcription activation assay, the yeast two-hybrid system, uses S. cerevisiae as a host cell for vectors that express the hybrid proteins. As described in Example I, a yeast host cell containing a reporter lacZ gene linked to a LexA operator sequence was used to identify specific interactions among the members of the Bcl-2 protein family. In the two-hybrid assay, the DNA-binding domain consisted of the LexA binding domain, which binds the LexA promoter, and the trans-activation domain consisted of the B42 acidic region. When the LexA domain was bridged to the B42 trans-activation domain through the interaction of members of the Bcl-2 protein family, transcription of the reporter lacZ gene was activated.

Although a transcription activation assay also can be performed using, for example, mammalian cells, the yeast two-hybrid system provides a particularly useful assay due to the ease of working with yeast and the speed with which the assay could be performed. As disclosed herein, the results obtained using the yeast two-hybrid system indicated, in part, that Bcl-2 can interact with the Bax protein to form Bcl-2/Bax heterodimers (see Table 1). These results confirm that the yeast two hybrid system reproduces interactions that can occur in vivo (Oltvai et al., supra, 1993).

The complete human Bcl-2 protein contains 239 amino acids (FIG. 3). Hybrid Bcl-2 proteins were constructed that contained amino acids 1 to 218 of the human Bcl-2 protein (Bcl-2(1-218)) fused to a LexA DNA-binding domain or a B42 trans-activation domain. The Bcl-2(1-218) protein, which is referred to herein as the "full-length" Bcl-2 protein, in fact lacks C-terminal residues 219 to 239, which include the amino acids that form the transmembrane domain of Bcl-2. Coexpression of nucleic acids encoding the LexA/Bcl-2(1-218) and B42/Bcl-2(1-218) hybrid proteins resulted in transcriptional activation of the lacZ reporter gene linked to the LexA operator (see Table 1). These results indicate that amino acids 1 to 218 of Bcl-2 form an appropriate secondary structure that allows Bcl-2 proteins to interact with each other to form a Bcl-2/Bcl-2 homodimer and provide the first experimental evidence that Bcl-2 can homodimerize with itself.

In order to identify further the regions of Bcl-2 that are required for homodimerization, constructs were prepared that encoded LexA and B42 hybrids containing amino acids 1 to 81 or 83 to 218 of Bcl-2. Transcription of the reporter gene was observed when the LexA/Bcl-2(83-218) and B42/Bcl-2(1-218) hybrids were coexpressed in a yeast cell but not when the LexA/Bcl-2(83-218) hybrid was coexpressed with a B42/Bcl-2(83-218) hybrid (see Table 2). This result indicates that a structure formed by amino acids located within the N-terminus of Bcl-2 is required for a Bcl-2 protein to interact with Bcl-2(83-218). This result was confirmed by showing that a B42/Bcl-2(1-81) hybrid complemented a LexA/Bcl-2(1-218) hybrid and a LexA/Bcl-2(83-218) hybrid (Table 2). These results indicate that Bcl-2/Bcl-2 homodimer is formed by a head-to-tail interaction of the N-terminal region of one Bcl-2 protein with the C-terminal region of a second Bcl-2 protein.

The results presented herein also provide the first experimental evidence that Bcl-2 can form heterodimers with Bcl-2-related proteins. Nucleic acid sequences encoding various hybrids were constructed as described in Example I. Coexpression of the LexA/Bcl-2(1-218) hybrid with either B42/Bcl-X-L, B42/Bcl-X-S, B42/Mcl-1 or B42/Bax hybrids resulted in transcription of the lacZ reporter gene (Table 1). Furthermore, coexpression of a hybrid containing the N-terminal truncated Bcl-2 protein, LexA/Bcl-2(83-218), with B42/Bcl-X-L, B42/Bcl-X-S or B42/Bax hybrids resulted in transcription of the reporter gene (Table 2). Thus, like Bcl-2, various Bcl-2-related proteins can interact with a region of Bcl-2 that contains amino acids 83 to 218. These results indicate that the structures formed by Bcl-2 and the Bcl-2-related proteins, which are required for the interaction of these proteins, are conserved among Bcl-2-related proteins. Furthermore, these results refute the previous suggestion that Bcl-2 does not bind to Bcl-X-S (Boise et al., supra, 1993).

As disclosed herein, Bcl-2-related proteins also can form homodimers and can form heterodimers with each other. For example, coexpression of a LexA/Bcl-X-L hybrid

TABLE 1

Summary of yeast two-hybrid assay results for Bcl-2 and Bcl-X-L proteins.

| | B42 | | | | | | | |
|---|---|---|---|---|---|---|---|---|
| LexA | Bcl-2 | Bcl-X-L | Bcl-X-S | Mcl-1 | Bax | clone 1 | clone 2 | Ras$^{Val12}$ |
| Bcl-2 | + | + | +++ | + | + | − | − | − |
| Bcl-X-L | + | + | +++ | + | + | − | − | − |
| c-raf | − | − | − | − | − | − | − | ++ |
| Lamin | − | − | − | − | − | − | − | − |
| Fas | − | − | − | − | − | − | − | − |

TABLE 2

Analysis of interactions of Bcl-2 deletion mutants by two-hybrid assay.

| | B42 | | | | | | | | |
|---|---|---|---|---|---|---|---|---|---|
| LexA | Bcl-2 | Bcl-2 (83–218) | Bcl-2 (1–81) | Bcl-X-L | Bcl-X-S | Bax | Mcl-1 | clone 1 | clone 2 |
| Bcl-2 | + | ++ | + | + | +++ | + | + | − | − |
| Bcl-2 (83–218) | ++ | − | ++ | ++ | ++ | − (PG) | + | − | − |
| Bcl-X-L | + | ++ | + | + | +++ | + | + | − | − |
| Fas | − | − | − | − | − | − (PG) | − | − | − |
| CD40 | nd | nd | − | nd | nd | nd | nd | − | − |
| c-raf | − | − | − | − | − | − (PG) | − | − | − |
| Lamin | − | − | − | − | − | − (PG) | − | − | − | with either B42/Bcl-2, B42/Bcl-X-L, B42/Bcl-X-S, B42/Bax or B42/Mcl-1 hybrids resulted in transcription of the reporter gene (Table 1). Thus, like Bcl-2, a Bcl-2-related protein such as Bcl-X-L, which shares 43% homology with Bcl-2, can form homodimers with itself as well as heterodimers with other members of the Bcl-2 protein family.

Although the interactions observed using the yeast two-hybrid system can be due to nonspecific binding, this is unlikely since hybrids formed using irrelevant proteins did not interact with a Bcl-2 hybrid and did not activate transcription in this assay (see, for example, Tables 1 and 2; "Fas," "CD40," "c-raf" and "lamin"). The interactions described herein also can be mediated by conserved yeast proteins, which are involved in yeast cell death. An effect due to conserved yeast proteins, however, would not affect the significance of the results because the same types of interactions likely would occur in mammalian cells (see below).

The invention also provides a drug screening assay useful for identifying agents that alter an interaction among proteins involved in cell death. Agents that alter interactions of Bcl-2 and Bcl-2-related proteins can be useful for increasing or decreasing the level of apoptosis in a cell.

A transcription activation assay such as the yeast two hybrid system is useful as a screening assay to identify effective agents that alter interactions among the Bcl-2 protein family. As used herein, the term "agent" means a chemical or biological molecule such as a simple or complex organic molecule, a peptide, a protein or an oligonucleotide. An "effective agent" is an agent that, in fact, alters an interaction of proteins involved in apoptosis. A transcription activation assay can be used to screen a panel of agents to identify an effective agent, which can be useful for increasing or decreasing apoptosis in a cell.

An effective agent can be identified by detecting an altered level of transcription of a reporter gene. For example, the level of transcription of a reporter gene due to the bridging of a DNA-binding domain and transactivation domain by Bcl-2 or Bcl-2-related proteins can be determined in the absence and in the presence of an agent. An effective agent that increases the interaction between members of the Bcl-2 protein family can be identified by an increased level of transcription of the reporter gene as compared to the control level of transcription in the absence of the agent.

For example, the interaction can be the binding of a Bcl-2 hybrid with a Bax hybrid. Oltvai et al., supra, (1993) report that cells characterized by having a relatively high number of Bax/Bax homodimers undergo a relatively high level of apoptotic death. However, overexpression of Bcl-2 in such cells results in the formation of Bcl-2/Bax heterodimers and a corresponding decreased level of apoptosis in the cells. These results suggest that an interaction of Bcl-2 and Bax, in part, regulates cell death. An agent that effectively increases the interaction of Bcl-2 and Bax, as detected by increased transcription of the reporter gene in a two-hybrid assay, can be used to decrease the level of apoptosis in a cell. Such an effective agent can be particularly useful as a medicament for treating a patient suffering from a disease characterized by a high level of apoptosis such as a neurodegenerative disease. Such an agent also can be useful, for example, to prolong the time a cell such as a hybridoma cell can survive in culture and, therefore, improve bioproduction yields in industrial tissue culture applications.

An effective agent that decreases the interaction of members of the Bcl-2 protein family also can be identified, in this case by detecting a decreased level of transcription of a reporter gene as compared to the level of transcription in the absence of the agent. For example, an agent that decreases the interaction of Bcl-2 and Bax in a cell can increase the level of apoptosis in the cell. Since, as disclosed herein, Bcl-2 binding to Bax can neutralize Bax-induced cell death, an effective agent as described above can be useful, for example, to increase the level of apoptosis of a cancer cell, which is characterized by having a decreased level of apoptosis as compared to its normal cell counterpart. Thus, effective agents identified using the methods described herein are particularly useful as medicaments to increase or decrease the level of apoptosis in a cell in a subject.

The expression of various Bcl-2-related proteins is tissue-specific (Negrini et al, Cell 49:455–563 (1987); Lin et al., J. Immunol. 151:1979–1988 (1988); Boise et al., supra, 1993; Oltvai et al., susupra 993). For example, Bcl-2 is not present in all cell types that undergo apoptosis. Thus, while Bcl-2 can regulate apoptosis in some cells, a Bcl-2-related protein such as Bcl-X-L may regulate apoptosis in a cell that lacks Bcl-2. It often can be difficult, however, to establish particular cell types in culture. An additional advantage of using the yeast two hybrid system is that it provides a means to screen and identify effective agents that alter the interaction of tissue-specific Bcl-2-related proteins without requiring that the specific cell type be cultured in vitro. Thus, the yeast two hybrid system allows for the identification of effective agents that can precisely regulate cell death in tissue-specific and therapeutically useful ways.

In some cases, an agent may not be able to cross the yeast cell wall and, therefore, cannot enter the yeast cell to alter an interaction among members of the Bcl-2 protein family. The use of yeast spheroplasts, which are yeast cells that lack a cell wall, can circumvent this problem (Smith and Corcoran, In *Current Protocols in Molecular Biology* (ed. Ausubel et al.; Green Publ., New York 1989), which is incorporated herein by reference). In addition, a potentially effective agent, upon entering a cell, may require "activation" by a cellular mechanism, which may not be present in yeast. Activation of an agent can include, for example, metabolic processing of the agent or a modification such as phosphorylation of the agent, which can be necessary to convert the agent into an effective agent. In this case, a mammalian cell line can be used to screen a panel of agents. A transcription assay such as the yeast two-hybrid system described in Example I can be adapted for use in mammalian cells using well known methods (Fearon et al., *Proc. Natl. Acad. Sci., USA* 89:7958–7962 (1992), which is incorporated herein by reference; see, also, Sambrook et al., *Molecular Cloning: A laboratory manual* (Cold Spring Harbor Laboratory Press 1989), and Ausubel et al., *Current Protocols in Molecular Biology* (Green Publ., New York 1989), each of which is incorporated herein by reference).

The invention further provides a method for identifying novel proteins that are involved in a cell death pathway. The invention provides, for example, a yeast cell line that expresses a mammalian Bax (yeast/mBax cells) such as a human or murine Bax protein and, as a result, does not grow in culture. The yeast/mBax cell can express a stably transformed mammalian Bax gene, which can be integrated into the yeast genome, or a transiently expressed mammalian Bax gene, each of which can be co-transformed with one or more other nucleic acid sequences. As used herein, the term "transformed" as applied to yeast cells is equivalent to the term "transfection" as applied to mammalian cells.

A LexA/mBax hybrid was produced from a nucleic acid sequence that encodes a LexA-murine Bax fusion protein, the expression of which was controlled by the alcohol dehydrogenase (ADH) promoter. The ADH promotor is a strong constitutive promoter as compared to the weaker inducible Gal promoter that was used to express the hybrids discussed above. Expression of the LexA/mBax hybrid in yeast cells suppressed colony formation of the cells (see Table 3).

In order to determine whether the inability of yeast/mBax cells to grow in culture was due to Bax-induced cell death, yeast/mBax cells were transformed with galactose-inducible nucleic acid sequences encoding B42/Bcl-2, B42/Bcl-X-L or B42/Mcl-1, each of which can bind Bax. As shown in Table 3, transfection of yeast/mBax cells with each of these constructs resulted in galactose-dependent restoration of cell growth. Thus, coexpression in a yeast cell of Bax with a protein such as Bcl-2 or a Bcl-2-related protein, which can bind Bax, inhibits Bax-induced death in yeast. These experiments provide the unexpected results that the effect of a murine Bax protein in yeast cells and the regulation of Bax-induced yeast cell death by Bcl-2 and Bcl-2-related proteins are similar to the actions of these proteins in mammalian cells. These results also provide the first indication that yeast, which are unicellular organisms, undergo a type of cell death that is mechanistically related to apoptosis.

In contrast, the deletion mutant Bcl-2 proteins, Bcl-2(1-81) and Bcl-2(83-218), failed to abrogate the suppressive effect of LexA/Bax on colony formation. Thus, either a structure formed by the entire Bcl-2 protein is required to bind Bax and down-regulate its action or the way. A mammalian Bax can be expressed as a fusion protein as described above and, if desired, its interactions can be examined using the two-hybrid assay. However, the use of a Bax fusion protein is not required for Bax-induced yeast cell death. Thus, the bax gene can be linked to any promotor that is expressed at a sufficiently high level in yeast cells to result in Bax-induced cell death.

Since a common, conserved cell death pathway is shared between yeast and mammalian cells, yeast/mBax cells provide a system for identifying other mammalian cell proteins involved in this cell death pathway. For example, yeast/mBax cells can be transformed with a mammalian cell-derived cDNA expression library. Expression of a cDNA encoding a Bcl-2-related protein that inhibits Bax-induced yeast cell death can be identified by detecting the formation of yeast/mBax cell colonies.

In some cases, a yeast/mBax cell that forms a colony following transformation with a cDNA library may express only a Bax protein and, therefore, falsely indicate that a cDNA encoding a protein that inhibits Bax-induced cell death is present in the yeast cell. Such "false negative" results can be identified by expressing the Bax protein and the proteins encoded by the transformed cDNA as fusion proteins useful in the two-hybrid assay. Thus, while such false negative yeast may survive, such a yeast cell would not show transcriptional activation of a reporter gene using the two-hybrid assay. Such false negative surviving yeast can be useful, however, to identify, for example, a spontaneous

TABLE 3

Neutralization of Bax activity by Bcl-2, Bcl-X-L, and Mcl-1.

| LexA | Media | B42 | | | | | | | |
|---|---|---|---|---|---|---|---|---|---|
| | | Bcl-2 | Bcl-X-L | Bcl-X-S | Mcl-1 | Bcl-2 (83–218) | Bcl-2 (1–81) | clone 1 | Lamin |
| Bax (sense) | Galactose | + $(2.8 \times 10^2)$ | + $(3.0 \times 10^2)$ | − (10) | + $(2.9 \times 10^2)$ | − (16) | − (19) | − (9) | − (8) |
| | Glucose | − (1) | − (5) | − (3) | − (1) | − (10) | − (10) | − (15) | − (7) |
| Bax (anti-sense) | Galactose | $1.2 \times 10^3$ | nd | nd | nd | nd | nd | nd | $2.2 \times 10^3$ |
| | Glucose | $6.6 \times 10^2$ | nd | nd | nd | nd | nd | nd | $2.2 \times 10^3$ | domain of Bcl-2 that binds Bax is contained in one region of Bcl-2 such as an amino acid sequence within Bcl-2(1-81), whereas the domain that mediates the Bcl-2 effector function on Bax is present within the Bcl-2(83-218) region. The expression of Bcl-X-S, which is a dominant inhibitor of Bcl-2, also failed to abrogate Bax-induced yeast cell death. Since Bcl-X-S lacks amino acids 126 to 188 as compared to Bcl-2 (FIG. 3), a structure formed by these amino acids must be required for Bcl-X-S to interact with Bax or to functionally neutralize Bax function. In contrast, the deleted region of Bcl-X-S is not required for binding to Bcl-2 or Bcl-X-L (Table 1).

The finding that human Bax protein has a lethal effect in S. cerevisiae and that Bax-induced lethality is modulated by Bcl-2 and Bcl-2-related proteins in a similar manner as occurs in mammalian cells indicates that a conserved cell death pathway exists in eukaryotic cells. The presence of such a conserved cell death pathway in yeast provides a useful system for identifying mammalian and yeast proteins that can be Bcl-2-related proteins or can be upstream activators or downstream effectors of Bax activity in the cell death pathway.

The yeast/mBax cells provide a system to identify mammalian cell proteins that are involved in a cell death pathmutation in the yeast cell that allows the cell to avoid Bax-induced cell death. Such a mutant yeast cell can be examined as described below.

The role of Bax in cell death is one step in a cell death pathway. Thus, transformation of yeast/mBax cells as described above also can identify upstream activators and downstream effectors of Bax activity. As used herein, the term "downstream effector" means a protein that is required in a cell death pathway and the expression of which is required by Bax to induce cell death. As used herein, the term "upstream activator" means a protein that can "activate" or render functional the Bax protein in a cell or that can activate expression of a bax gene such that Bax then can induce a downstream cell death pathway.

A cDNA encoding an upstream activator or downstream effector of Bax can be identified by selecting yeast/mBax cells that can form colonies following transformation with a nucleic acid sequence present in a mammalian cell-derived cDNA library. Following selection of a yeast cell colony, a mammalian cell-derived cDNA can be isolated from the yeast/mBax cells and sequenced and the amino acid sequence of the upstream activator or downstream effector can be determined. Using this method, mammalian proteins that are involved in the Bax cell death pathway can be identified.

The yeast/mBax cells also are useful for identifying yeast proteins that are involved in the Bax cell death pathway. For example, yeast/mBax cells can be exposed to a mutagenic agent such as ethylmethanesulfonate or ionizing radiation and mutant yeast/mBax cells that form colonies in culture can be selected. Similarly, yeast cells that have a spontaneous mutation as described above can be selected. The mutant cells that form colonies likely will contain a mutation either in the gene encoding mBax or in a yeast gene encoding a member of the Bcl-2 protein family or encoding an upstream activator or downstream effector of human Bax. Using established methods of yeast genetic analysis (Guthrie and Fink, In *Meth. Enzymol.*, vol. 194 "Guide to Yeast Genetics and Molecular Biology (Academic Press 1992), complementation groups can be identified and nucleic acids encoding yeast proteins involved in the Bax cell death pathway can be identified. The amino acid sequences of these proteins can be determined and can be compared to known protein sequences.

Nucleic acid sequences that encode yeast proteins involved in cell death, as identified by the mutagenesis method described above, can be used to screen a mammalian cell cDNA library under conditions that allow cross-hybridization of a yeast nucleic acid with a homologous mammalian nucleic acid sequence. This method provides an additional means for identifying mammalian proteins involved in the Bax cell death pathway.

The following examples are intended to illustrate but not limit the present invention.

EXAMPLE I

PROTEINS INVOLVED IN REGULATING CELL DEATH INTERACT IN THE YEAST TWO-HYBRID SYSTEM

This example provides a method for identifying protein-protein interactions among proteins involved in regulating cell death.

A. Plasmid constructions:

This section describes methods for obtaining DNA sequences encoding various proteins suspected of being involved in regulating cell death and for constructing plasmids containing the DNA sequences such that the encoded proteins are expressed as fusion proteins (hybrids) that are useful in the yeast two-hybrid assay.

1. Cloning of murine Bax and human Mcl-1

A cDNA encoding human Mcl-1 was cloned by reverse transcription of total RNA isolated from U-937 cells (ATCC CRL 1593). RNA was reverse-transcribed using recombinant Moloney leukemia virus reverse transcriptase (Superscript; Gibco/BRL) according to the procedure suggested by the manufacturer. A combination of random oligodeoxynucleotide hexamer primers and a primer that is complementary to a region 3' of the open reading frame of mcl-1 (5'-CATAATCCTCTTGCCACTTGC-3'; SEQ ID NO: 1) was used (Kozopas et al., *Proc. Natl. Acad. Sci. USA* 90:3516–3520 (1993), which is incorporated herein by reference).

The first strand cDNA sequence was amplified by the polymerase chain reaction (PCR) using Vent™ polymerase (New England Biolabs; Beverly, Mass.) and a 5' primer containing a Sac I site (underlined) flanking the initiation codon (5'CA<u>GAGCTC</u>GCAATGTTTGGCCTCA-3'; SEQ ID NO: 2) and a reverse primer complementary to sequences downstream of the mcl-1 stop codon (5'-GAAGTTACAGCTTGGAGTCC-3'; SEQ ID NO: 3). The 1.1 kilobase (kb) PCR product was digested with Sac I and Hinc II and cloned into the Bluescript plasmid, pSKII (Stratagene; San Diego Calif.). The mcl-1 cDNA sequence was confirmed to be error free by DNA sequencing.

A cDNA encoding the entire open reading frame of a murine Bax protein was cloned by reverse transcription of mouse kidney mRNA. Sequences were amplified by PCT using bax-specific forward (5'-G<u>GAATTC</u>GCGGTGATGGACGGGTCCGG-3'; SEQ ID NO: 4) and reverse (5'-G<u>GAATTC</u>TCAGGCCCATCTTCTTCCAGA-3'; SEQ ID NO: 5) primers containing Eco RI sites (underlined) (Oltari et al., *Cell* 74:609–619 (1993), which is incorporated herein by reference). The PCR product was digested with Eco RI and subcloned into pSKII. The bax cDNA sequence was confirmed to be error free by DNA sequencing.

2. Plasmid vectors

Two plasmids, pEG202 and pJG4-5, were used for expressing fusion proteins in the yeast two-hybrid assay (Zervous et al., *Cell* 72:223–232 (1993); Gyuris et al., *Cell* 75:791–803 (1993); Golemis et al., *In Current Protocols in Molecular Biology* (ed. Ausubel et al.; Green Publ.; New York 1993) each of which is incorporated herein by reference). Plasmid pEG202 was derived from plasmid LexA202+PL (Ruden et al., *Nature* 350:250–252 (1991); Ma and Ptashne, *Cell* 51:113–119 (1987), each of which is incorporated herein by reference) and contains additional unique polylinker sites for cloning. Plasmid pEG202 was created by cleaving LexA202+PL at the unique Sal I site, which is present in the polylinker downstream of LexA, and inserting a 22-mer that regenerates the Sal I site and also contains novel Nco I, Not I and Xho I sites.

Figure 1:
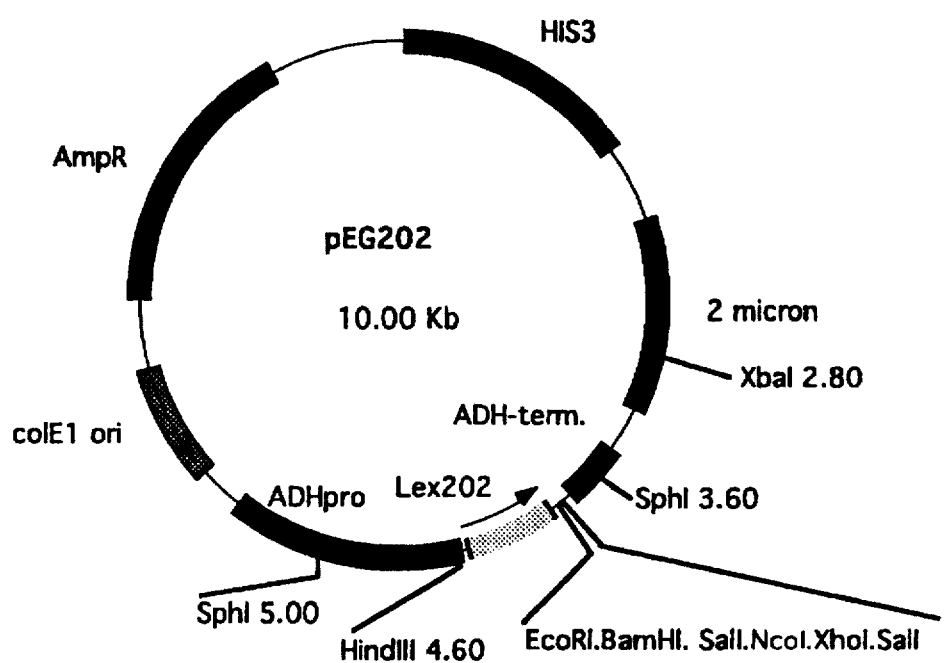
FIG. 1 provides a map of plasmid pEG202, which was used to produce LexA fusion proteins. The plasmid contains a gene that confers ampicillin resistance in bacteria (AmpR) and a colE1 origin of replication, which allows the plasmid to replicate in bacteria. The plasmid also contains a gene that allows a yeast cell containing the plasmid to grow in the absence of histidine (HIS3) and the yeast 2 micron origin of replication, which allows replication in yeast.

The 22-mer was constructed by synthesizing two oligonucleotides, 5'-TCGACCATGGCGGCCGCTCGAG-3' (SEQ ID NO: 6) and 5'-TCGACTCGAGCGGCCGCCATGG-3' (SEQ ID NO: 7) and allowing the complementary regions of the oligonucleotides to anneal. The 22-mer was ligated into the Sal I site of LexA202+202 to create pEG202. As shown in FIG. 1, pEG202 also contains the yeast 2 micron origin of replication and a histidine selectable marker. Expression of the LexA-fusion cassette is from the strong constitutive ADH1 promotor. Insertion of a cDNA encoding an open reading frame into the Eco RI, Bam HI, Sal I, Nco I, Not I or Xho I site of pEG202 results in the production of a LexA-profusion protein.

The plasmid pJG4-5 was derived from a pUC plasmid and contains a galactose inducible promotor (FIG. 2). Insertion of a cDNA encoding an open reading frame into the Eco RI or Xho I site results in the production of a fusion protein with the B42 trans-activation domain and containing an SV40 nuclear localization signal and a hemagglutinin epitope tag (Zervous et al., supra, 1993; Gyuris et al., supra, 1993).

3. Preparation of vectors encoding hybrid proteins

The cDNA sequences encoding murine Bax and human Mcl-1 and cDNA sequences encoding human Bcl-2 (from pSKII-bcl-2α; Tanaka et al., *J. Biol. Chem.* 268:10920–10926 (1993), which is incorporated herein by reference), human Bcl-X-L and Bcl-X-S (Boise et al., supra, 1993) and human Fas-1/APO (Itoh et al., *Cell* 66:233–243 (1991), which is incorporated herein by reference) were modified by PCR mutagenesis (Higuchi et al., In *PCR Protocols* (ed. Innes et al.; Academic Press; San Diego Calif. 1990), which is incorporated herein by reference) using the primers described below and subcloned in frame into the two-hybrid plasmids, pEG202 and pJG4-5. In order to prevent potential targeting of expressed proteins to the nucleus, sequences corresponding to the transmembrane domains of Bcl-2, Bcl-X-L, Bcl-X-S, Bax and Mcl-1 were deleted (FIG. 3) and a stop codon was inserted at the end of the open reading frame.

As described above, pEG202 utilizes an ADH promoter to constitutively drive expression of a fusion protein containing an N-terminal LexA DNA binding domain. All cDNA sequences were subcloned into the Eco RI site of pEG202, in-frame with the upstream LexA sequences. Forward and reverse primers, which contained an Eco RI site (underlined) or Bcl I site (italics), were as follows (bold indicates DNA encoding stop codon; TCA): (i) Bcl-2 (amino acids (aa) 1 to 218) (5'-GGAATTCATGGCGCACGCTGGGAGAAC-3'; SEQ ID NO: 8) AND (5'-TGATCACTTCAGAGACAGCCAC-3'; SEQ ID NO: 9); (ii) Bcl-X-L (aa 1 to 212) and Bcl-X-S (aa 1 to 149) (5'-GGAATTCATGTCTCAGAGCAACCGG-3'; SEQ ID NO: 10) and (5'-CTGATCAGCGGTTGAAGCGTTCCTG-3'; SEQ ID NO: 11); (iii) Bax (aa 1 to 171) (5'-GGAATTCGCGGTGATGGACGGGTCCGG-3'; SEQ ID NO: 12) and (5'-GGAATTCTCAGCCCATCTTCTTCCAGA-3'; SEQ ID NO: 13); and (iv) Fas/APO-1 (aa 191 to 335) (5'-GGAATTCAAGAGAAAGGAAGTACAG-3'; SEQ ID NO: 14) and (5'-TGATCACTAGACCAAGCTTTGGAT-3'; SEQ ID NO: 15).

For the cDNA encoding Mcl-1, sequences corresponding to the 3' portion of the open reading frame were amplified by PCR from the first strand cDNA (above) using a forward primer (5'-AGAATTCACCTTACGACGGGTTGG-3'; SEQ ID NO: 16), which corresponds to amino acid 212, and a reverse primer (5'-CGAATTCACCTGATGCCACCTTCTAG-3'; SEQ ID NO: 17), which ends at amino acid 329. The resulting 0.37 kb PCR fragment was cloned into the Eco RI site of pSKII, then the plasmid construct was digested with Xho I and Sma I to liberate a 0.28 kb fragment that lacks the transmembrane region of Mcl-1.

The full length PCR-generated mcl-1 cDNA (described above) was subcloned into pUC18. The pUC/mcl-1 plasmid was digested with Xho I and Hinc II to release a 0.34 kb fragment of the 3' open reading frame, which contains the transmembrane region. The plasmid was purified from the 0.34 kb fragment and the 0.28 kb Xho I/Sma I fragment, which lacks the transmembrane region, was inserted to reconstitute an mcl-1 cDNA encoding an Mcl-1 protein lacking the transmembrane region. The resulting plasmid was digested with Eco RI and the 1.0 kb fragment representing amino acids 1 to 329 of Mcl-1 was subcloned into the Eco RI site of pEG202 or pJG4-5.

The pJG4-5 plasmid utilizes a galactose-inducible promoter to inducibly drive expression of fusion proteins containing an N-terminal B42 trans-activation domain. For subcloning into pJG4-5, the cDNA inserts in pEG202 were released by digestion with Eco RI and Xho I, then subcloned between the Eco RI and Xho I sites of pJG4-5, in frame with the upstream B42 sequences. The plasmids pEG202/lamin C and pJG4-5/lamin C were constructed from pBMT116-lamin C (Vojtek et al., Cell 74:205-214 (1993), which is incorporated herein by reference).

Plasmids containing a C-terminal Bcl-2 deletion mutant, pEG202/Bcl-2(1-81) and pJG4-5/Bcl-2(1-81), were constructed by digesting pEG202/Bcl-2 or pJG4-5/Bcl-2 with Sac II/Bam HI or Sac II/Xho I, respectively, blunting the ends of the digested plasmids using T4 DNA polymerase and religating the blunt-ended plasmids. Plasmids containing an N-terminal Bcl-2 deletion mutant, pEG202/Bcl-2(83-218) or pJG4-5/Bcl-2(83-218), were constructed by digesting pEG202/Bcl-2 or pJG4-5/Bcl-2 with Sac II and Eco RI, blunting the ends with T4 DNA polymerase and religating the blunt-ended plasmids.

The structures of the regions of Bcl-2, Bax, Bcl-X-L, Bcl-X-S and Mcl-1 that were subcloned into pEG202 and pJG4-5 are shown in FIG. 3. Proper construction of all plasmids and the absence of PCR-generated errors were verified in every case by DNA sequence analysis.

B. Yeast two-hybrid assay:

This section describes methods for performing the yeast two-hybrid assay.

1. Yeast strain and reporter gene

S. cerevisiae strain EGY191 was used as the host for the two-hybrid assays. Strain EGY191 cells have a MATα trp1 ura3 his3 LEU2::pLexAop1-LEU2 genotype. Yeast were grown in YPD medium (1% yeast extract/2% polypeptone/ 2% glucose). Burkholder's minimal medium (Tohe et al., J. Bacteriol. 113:727-738 (1973), which is incorporated herein by reference) fortified with appropriate amino acids was used for preparation of high phosphate medium (0.15% KH$_2$PO$_4$) unless otherwise indicated.

Plasmid DNA was transformed into yeast cells by the LiCl method (Schiestl et al., Curr. Genet. 16:339-346 (1989), which is incorporated herein by reference) and the cells were grown in complete minimal medium lacking uracil, tryptophan or histidine as necessary to select for the presence of pSH, pJG or pEG derived plasmids, respectively. Following expression of various fusion proteins, yeast cell extracts were prepared using a spheroplast method (Smith and Corcoran, 1989) and expression of LexA- or B42-fusion proteins was confirmed by immunoblot assays using a polyclonal anti-LexA antiserum, which can be prepared as described by Brent and Ptashne (Nature 312:612-615 (1984), which is incorporated herein by reference), or an anti-HA1 monoclonal antibody (clone 12CA5; Boehringer Mannheim; Indianapolis Ind.), respectively.

EGY191 yeast cells were stably transformed with pSH18-34, which contains the lac Z gene linked to a LexA operator sequence (FIG. 4) (Hanes and Brent, Cell 57:1275-1283 (1989) and Hanes and Brent, Science 251:426-430 (1991), each of which is incorporated herein by reference). Plasmid pSH18-34, which contains 8 copies of the LexA operator sequence, was constructed by inserting two 78 base pair oligonucleotides formed by annealing (5'-TCGACTGCTGTATATAAAACCAGTGGT-TATATGTACAGTACTGCTGTATATAAAACC AGTGGTTATATGTACAGTACG-3'; SEQ ID NO: 18) and ( 5 ' - TCGACGTACTGTACATATAACCACTG-GTTTTATATACAGCAGTACTGTACATATAAC CACTGGTTTTATATACAGCAG-3'; SEQ ID NO: 19) into the Xho I site of plasmid pLR1Δ1 (West et al., Mol. Cell. Biol. 4:2467-2478 (1984), which is incorporated herein by reference). Each oligonucleotide contains four binding sites for the LexA DNA binding protein. A yeast cell containing pSH18-34 can be identified by its ability to grow in medium lacking uracil.

In the presence of galactose, the binding of a transcriptionally competent LexA binding protein to the LexA operator in pSH18-34 resulted in expression of the lacZ gene and production of β-galactosidase. Transcriptional activation was identified by performing β-galactosidase assays on plates or on filters. For plate assays, yeast cells were spotted onto SD minimal medium plates lacking uracil, tryptophan and histidine and containing 2% glucose or 2% galactose and the chromogenic substrate, X-gal (5-bromo-4-chloro-3-indolyl β-D-galactopyranoside (Chien et al., *Proc. Natl. Acad. Sci., USA* 88:9578–9582 (1991), which is incorporated herein by reference). Filter assays were performed essentially as described by Breeden and Nasmyth (*Cold Spring Harbor Symp. Quant. Biol.* 50:643–650 (1985), which is incorporated herein by reference), except that Pall (East Hills N.Y.) nylon membranes were used. Z-buffer containing 25 μg/ml X-gal in N,N-dimethylformamide was used for measuring β-galactosidase activity. Filters were monitored for the presence of blue color reaction products at 0.5, 1, 2, 4 and 24 hr.

2. Homodimerization of Bcl-2

A LexA/Bcl-2 fusion protein containing amino acids 1 to 218 of the human Bcl-2 protein, lexA/Bcl-2(1-218), resulted in trans-activation of the lac Z reporter gene when it was co-expressed with a B42/Bcl-2(1-218) hybrid. These results indicate that amino acids 1 to 218 of the Bcl-2 protein are sufficient for Bcl-2/Bcl-2 homodimerization.

Bcl-2 deletion mutant proteins were constructed to identify regions of Bcl-2 that are required for Bcl-2/Bcl-2 homodimerization. A LexA/Bcl-2(83-218) hybrid complemented B42/Bcl-2(1-218) hybrids but not B42/Bcl-2(83-218) hybrids (Table 2). Thus, a Bcl-2 N-terminal deletion mutant was able to interact with the "full-length" Bcl-2(1-218) protein, but not with itself, to form a "homodimer." This result indicates that amino acid sequences located between residues 1 to 83 of the Bcl-2 protein are required for interacting with the Bcl-2(83-218) region.

In order to confirm that the Bcl-2(83-218) N-terminal deletion mutant binds to the Bcl-2(1-81) region, LexA and B42 constructs containing amino acids 1 to 81 of human Bcl-2 were prepared. The B42/Bcl-2(1-81) hybrid complemented both LexA/Bcl-2(1-218) and LexA/Bcl-2(83-218) hybrids (Table 2). Transcriptional activation induced by the complementation of the Bcl-2-related protein hybrids with the B42/Bcl-2(1-81) was specific and was not observed when the B42/Bcl-2(1-81) hybrid was coexpressed with the negative control hybrids, LexA/c-raf, LexA/lamin and LexA/Fas (Table 1). Thus, the N-terminal domain of one Bcl-2 protein interacts with the C-terminal region of a second Bcl-2 protein in a head-to-tail fashion to form a Bcl-2/Bcl-2 homodimer. Expression of the lexA/Bcl-2(1-81) hybrid, alone, caused non-specific transcription of the lacZ gene (Table 2) and, therefore, the converse experiments could not be performed. This non-specific transcriptional activation can be due to the ability of an acidic region of Bcl-2(1-81) to act as a trans-activation domain.

3. Interactions Among Members of the Bcl-2 Protein Family:

The two-hybrid system also was used to show that members of the Bcl-2 protein family can form homodimers and can form heterodimers with each other. Coexpression of the LexA/Bcl-2(1-218) hybrid with either B42/Bcl-X-L, B42/Bcl-X-S, B42/Mcl-1 or B42/Bax hybrids resulted in transcription of the lacZ reporter gene (Table 1), indicating that Bcl-2 can interact specifically with Bcl-2-related proteins to form heterodimers.

In addition, a LexA/Bcl-X-L hybrid complemented B42/Bcl-2, B42/Bcl-X-L, B42/Bcl-X-S, B42/Bax and B42/Mcl-1 fusion proteins but not B42 fusions with irrelevant proteins (Table 1). Thus, Bcl-X-L, which shares 43% homology with Bcl-2, can mediate similar interactions as Bcl-2 among the members of the Bcl-2 protein family. In addition, a B42/Bcl-X-L hybrid complements a LexA/Bcl-2 hybrid, but not LexA/c-raf, LexA/Lamin or LexA/Fas fusion proteins. These results again demonstrate the specificity of the interactions that occur among the members of the Bcl-2 protein family.

Coexpression of the LexA/Bcl-2(83-218) hybrid with a B42 hybrid containing either Bax, Bcl-X-L or Bcl-X-S also activated transcription of the reporter lacZ gene (Table 2). These results indicate that the amino acid sequences of these Bcl-2-related proteins that are necessary for interacting with the 83 to 218 region of Bcl-2 are conserved among these proteins.

EXAMPLE II

USE OF THE TWO-HYBRID ASSAY TO SCREEN FOR AGENTS THAT EFFECTIVELY ALTER THE INTERACTIONS OF MEMBERS OF THE BCL-2 PROTEIN FAMILY

This example describes a method for identifying an agent such as a drug that effectively alters an interaction between members of the Bcl-2 protein family.

The two-hybrid assay can be performed as described in Example I. Any of various hybrids can be expressed in a cell such as a yeast cell, provided that the cell contains a reporter gene and that the hybrids can bind to each other to activate transcription of the reporter gene.

The cells can be incubated in the presence of an agent suspected of being able to alter the binding of the hybrids to each other. An agent such as a drug that effectively alters an interaction of the hybrids can be identified by an increase or decrease, for example, in the intensity of the blue color produced due to transcription of a lacZ reporter gene. A control level of binding can be determined by identifying the level of transcription in the absence of the agent. Quantitative β-galactosidase assays also can be performed as described by Rose et al., *Proc. Natl. Acad. Sci., USA* 78:2460–2464 is (1981), which incorporated herein by reference.

The screening assay is particularly useful for screening a panel of agents to identify an effective agent. For screening a panel of agents, the assay can be performed in parallel in 96 well plates. Following incubation in the absence or presence of various agents or combinations of agents for an appropriate time, cell extracts can be prepared and β-galactosidase activity can be determined using either a filter assay as described in Example I or a soluble β-galactosidase assay using cell lysates as described by Rose et al., supra, 1981. Agents that effectively increase or decrease, as desired, binding of the hybrids can be identified by simple visual inspection of the filter or by quantitative spectrophotometry and effective agents can be selected.

EXAMPLE

MAMMALIAN BAX INDUCES CELL DEATH IN YEAST

This example demonstrates that expression of a murine Bax protein in yeast induces cell death in the yeast cells and that Bax-induced cell death can be abrogated by Bcl-2 and various Bcl-2-related proteins.

In the two-hybrid assay described in Example I, expression of a B42/Bax fusion protein under the control of the inducible Gal promoter often retarded yeast colony formation when cells were incubated in the presence of galactose (Table 3). In order to examine the specificity of this effect, a nucleic acid sequence encoding LexA/Bax fusion protein was placed under the control of the strong constitutive ADH promoter. In various assays, transformation of yeast cells with this construct resulted in a complete or nearly complete absence of colony formation on glucose plates, whereas transformation of cells with the same vector containing the bax cDNA cloned in a reverse (antisense) orientation had no effect on normal colony formation (Table 3). Thus, the expression of a murine Bax protein in yeast cells inhibits growth of the yeast cells.

In order to determine whether the Bax-induced yeast cell death was affected by coexpression of Bcl-2 or Bcl-2-related proteins, yeast cells were cotransformed with the LexA/Bax vector and with a galactose-inducible B42/Bcl-2, B42/Bcl-X-L or B42/Mcl-1 plasmid. Incubation of the cotransformed cells in the presence of galactose inhibited the effect of Bax and restored cell growth (Table 3). In contrast, expression of a B42/Bcl-X-S hybrid or a deletion mutant Bcl-2 protein, B42/Bcl-2(1-81) or B42/Bcl-2(83-218), failed to significantly abrogate the suppressive effects of LexA/Bax on colony formation (Table 3). Fusions of B42 to irrelevant proteins also failed to neutralize the inhibitory activity of LexA/Bax on colony formation (see Table 3; clone 1 and Lamin). Immunoblot assays confirmed that the effects described above were not due to quantitative differences in the expression of the various constructs (not shown).

These results indicate that the expression of murine Bax specifically inhibits the growth of yeast cells. The specificity of Bax-induced cell death is confirmed by the ability of Bcl-2 and Bcl-X-L, which are known suppressors of apoptotic death, to abrogate the effect of Bax, whereas Bcl-X-S, which is a dominant inhibitor of Bcl-2, failed to prevent Bax-induced cell death. Although Bax and Bcl-X-S can both bind to Bcl-2, the results presented herein suggest that these dominant inhibitors of Bcl-2 function affect different steps of a cell death pathway, as the expression of mammalian Bax can induce yeast cell death whereas Bcl-X-S expression does not inhibit yeast cell growth (not shown).

The observation that the binding of Bcl-2 to Bax and to Bcl-X-S can affect different steps of a cell death pathway provides a useful system for identifying agents that effectively alter cell death. Thus, as described above, an agent that can reduce or inhibit the formation of Bcl-2/Bax heterodimers can be useful for promoting cell death by increasing the level of unbound Bax in a cell. In contrast, an agent that reduces or inhibits the formation of Bcl-2/Bcl-X-S heterodimers can decrease the level of cell death by increasing the amount of unbound Bcl-2 in a cell, thereby allowing the free Bcl-2 to bind Bax and neutralize Bax activity.

These results also indicate that a cell death pathway that involves Bax and is regulated by Bcl-2 or Bcl-2-related proteins is conserved among eukaryotes as diverse as yeast and mice. Thus, the interactions detected using the two-hybrid system can be physiologically relevant as reflected by the ability members of the Bcl-2 protein family that bind Bax to abrogate Bax-induced cell death. As a result, the yeast/mBax system provides a means to identify other proteins involved in regulating cell death.

EXAMPLE IV

IDENTIFICATION OF NOVEL PROTEINS INVOLVED IN A CELL DEATH PATHWAY

This example describes methods of using a yeast/mBax cell for identifying proteins involved in a cell death pathway.

Yeast/mBax cells can be prepared by transforming a yeast cell with a vector that expresses a mammalian Bax protein as described in Example III. Yeast/mBax cells cannot form colonies in culture. A mammalian cell-derived cDNA library can be obtained using methods known in the art. In particular, the library can be cloned into a vector that permits expression of the cDNA sequence in a yeast cell.

Yeast/mBax cells can be transformed with the mammalian cell-derived cDNA library and plated in an appropriate medium. The formation of colonies indicates that the yeast/mBax cell contains a cDNA sequence encoding a protein that can inhibit Bax-induced cell death. Such colonies can be selected, the cDNA can be isolated and sequenced and the amino acid sequence can be derived and compared to known amino acid sequences. In this way, novel proteins involved in the Bax cell death pathway can be identified.

Although the invention has been described with reference to the examples provided above, it should be understood that various modifications can be made without departing from the spirit of the invention. Accordingly, the invention is limited only by the claims.

We claim:

1. A method of detecting a protein involved in a cell death pathway, comprising the steps of:

a. obtaining a cell that expresses an exogenous protein involved in a cell death pathway, wherein expression of said exogenous protein results in the death of said cell;

b. expressing in said cell a second protein that is suspected of being involved in a cell death pathway; and c. detecting the survival of said cell, wherein said survival indicates that said second protein is involved in a cell death pathway.

2. The method of claim 1, wherein said cell is a yeast cell.

3. The method of claim 1, wherein said exogenous protein is a Bax protein.

4. The method of claim 1, wherein said second protein is expressed from a recombinant nucleic acid.

5. The method of claim 1, wherein said second protein is a mutant protein.

* * * * *

UNITED STATES PATENT AND TRADEMARK OFFICE
CERTIFICATE OF CORRECTION

PATENT NO.   : 5,702,897
DATED        : December 30, 1997
INVENTOR(S)  : Reed et al.

It is certified that error appears in the above-identified patent and that said Letters Patent is hereby corrected as shown below:

Column 1,
Line 25, please delete "colon", replace therefor with -- common --.

Column 3,
Line 37, please delete "Scl-2", replace therefor with -- Bcl-2 --.

Column 8,
Line 15, please delete "susupra 993)", replace therefor with -- supra 1993) --.

Column 12,
Line 47, please delete "LexA-", replace therefor with -- LexA --.
Line 48, please delete "profusion", replace therefor with -- fusion --.

Column 13,
Lines 17, 20 and 27, please delete "TGATCA", replace therefor with -- *TGATCA* --.
Lines 24 and 35, please delete "TCA", replace therefor with -- TCA --.

Column 16,
Line 38, please delete "which", replace therefor with -- which is --.
Line 54, please delete "EXAMPLE", replace therefor with -- EXAMPLE III --.

Signed and Sealed this

Seventeenth Day of December, 2002

JAMES E. ROGAN
*Director of the United States Patent and Trademark Office*

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:1:

CATAATCCTC TTGCCACTTG C 2 1

( 2 ) INFORMATION FOR SEQ ID NO:2:

( i ) SEQUENCE CHARACTERISTICS:
( A ) LENGTH: 24 base pairs ( B ) TYPE: nucleic acid
( C ) STRANDEDNESS: single
( D ) TOPOLOGY: linear ( x i ) SEQUENCE DESCRIPTION: SEQ ID NO:2:

CAGAGCTCGC AATGTTTGGC CTCA 24

( 2 ) INFORMATION FOR SEQ ID NO:3:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:3:

GAAGTTACAG CTTGGAGTCC 20

( 2 ) INFORMATION FOR SEQ ID NO:4:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( x i ) SEQUENCE DESCRIPTION: SEQ ID NO:4:

GGAATTCGCG GTGATGGACG GGTCCGG 27

( 2 ) INFORMATION FOR SEQ ID NO:5:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( x i ) SEQUENCE DESCRIPTION: SEQ ID NO:5:

GGAATTCTCA GGCCCATCTT CTTCCAGA 28

( 2 ) INFORMATION FOR SEQ ID NO:6:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( x i ) SEQUENCE DESCRIPTION: SEQ ID NO:6:

TCGACCATGG CGGCCGCTCG AG 22

( 2 ) INFORMATION FOR SEQ ID NO:7:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( x i ) SEQUENCE DESCRIPTION: SEQ ID NO:7:

TCGACTCGAG CGGCCGCCAT GG 22

( 2 ) INFORMATION FOR SEQ ID NO:8:

( i ) SEQUENCE CHARACTERISTICS:
( A ) LENGTH: 27 base pairs
( B ) TYPE: nucleic acid
( C ) STRANDEDNESS: single ( D ) TOPOLOGY: linear ( x i ) SEQUENCE DESCRIPTION: SEQ ID NO:8:

GGAATTCATG GCGCACGCTG GGAGAAC                                          27

( 2 ) INFORMATION FOR SEQ ID NO:9:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:9:

TGATCACTTC AGAGACAGCC AC                                               22

( 2 ) INFORMATION FOR SEQ ID NO:10:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:10:

GGAATTCATG TCTCAGAGCA ACCGG                                            25

( 2 ) INFORMATION FOR SEQ ID NO:11:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:11:

CTGATCAGCG GTTGAAGCGT TCCTG                                            25

( 2 ) INFORMATION FOR SEQ ID NO:12:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:12:

GGAATTCGCG GTGATGGACG GGTCCGG                                          27

( 2 ) INFORMATION FOR SEQ ID NO:13:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:13:

GGAATTCTCA GCCCATCTTC TTCCAGA                                          27

( 2 ) INFORMATION FOR SEQ ID NO:14:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:14:

GGAATTCAAG AGAAAGGAAG TACAG                                                    25

( 2 ) INFORMATION FOR SEQ ID NO:15:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

TGATCACTAG ACCAAGCTTT GGAT                                                     24

( 2 ) INFORMATION FOR SEQ ID NO:16:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

AGAATTCACC TTACGACGGG TTGG                                                     24

( 2 ) INFORMATION FOR SEQ ID NO:17:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

CGAATTCACC TGATGCCACC TTCTAG                                                   26

( 2 ) INFORMATION FOR SEQ ID NO:18:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

TCGACTGCTG TATATAAAAC CAGTGGTTAT ATGTACAGTA CTGCTGTATA TAAAACCAGT              60

GGTTATATGT ACAGTACG                                                            78

( 2 ) INFORMATION FOR SEQ ID NO:19:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

TCGACGTACT GTACATATAA CCACTGGTTT TATATACAGC AGTACTGTAC ATATAACCAC              60

TGGTTTTATA TACAGCAG                                                            78

( 2 ) INFORMATION FOR SEQ ID NO:20:

( i ) SEQUENCE CHARACTERISTICS:
        ( A ) LENGTH: 239 amino acids
        ( B ) TYPE: amino acid
        ( D ) TOPOLOGY: linear ( x i ) SEQUENCE DESCRIPTION: SEQ ID NO:20:

```
Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35              40                  45

Phe Ser Ser Gln Pro Gly His Thr Pro His Thr Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
                100                 105                 110

Ala Glu Met Ser Arg Gln Leu His Leu Thr Pro Phe Thr Ala Arg Gly
            115                 120                 125

Arg Phe Ala Thr Val Val Glu Glu Leu Phe Arg Asp Gly Val Asn Trp
        130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235
```

( 2 ) INFORMATION FOR SEQ ID NO:21:

( i ) SEQUENCE CHARACTERISTICS:
( A ) LENGTH: 236 amino acids
( B ) TYPE: amino acid
( D ) TOPOLOGY: linear ( x i ) SEQUENCE DESCRIPTION: SEQ ID NO:21:

```
Met Ala Gln Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Thr
            20                  25                  30

Gly Asp Glu Asp Ser Ala Pro Leu Arg Ala Ala Pro Thr Pro Gly Ile
        35              40                  45

Phe Ser Phe Gln Pro Glu Ser Asn Arg Thr Pro Ala Val His Arg Asp
    50                  55                  60

Thr Ala Ala Arg Thr Ser Pro Leu Arg Pro Leu Val Ala Asn Ala Gly
65                  70                  75                  80

Pro Ala Leu Ser Pro Val Pro Pro Val Val His Leu Thr Leu Arg Arg
                85                  90                  95

Ala Gly Asp Asp Phe Ser Arg Arg Tyr Arg Arg Asp Phe Ala Glu Met
            100                 105                 110

Ser Ser Gln Leu His Leu Thr Pro Phe Thr Ala Arg Gly Arg Phe Ala
```

|     |     |     | 115 |     |     |     | 120 |     |     |     | 125 |     |     |
| --- | --- | --- | --- | --- | --- | --- | --- | --- | --- | --- | --- | --- | --- |
| Thr | Val 130 | Val | Glu | Glu | Leu | Phe 135 | Arg | Asp | Gly | Val | Asn 140 | Trp | Gly | Arg | Ile |
| Val 145 | Ala | Phe | Phe | Glu | Phe 150 | Gly | Gly | Val | Met | Cys 155 | Val | Gly | Ser | Val | Asn 160 |
| Arg | Glu | Met | Ser | Pro 165 | Leu | Val | Asp | Asn | Ile 170 | Ala | Leu | Trp | Met | Thr 175 | Glu |
| Tyr | Leu | Asn | Arg 180 | His | Leu | His | Thr | Trp 185 | Ile | Gln | Asp | Asn | Gly 190 | Gly | Trp |
| Asp | Ala | Phe 195 | Val | Glu | Leu | Tyr | Gly 200 | Pro | Ser | Met | Arg | Pro 205 | Leu | Phe | Asp |
| Phe | Ser | Trp 210 | Leu | Ser | Leu | Lys 215 | Thr | Leu | Leu | Ser | Leu 220 | Ala | Leu | Val | Gly |
| Ala 225 | Cys | Ile | Thr | Leu | Gly 230 | Ala | Tyr | Leu | Gly | His 235 | Lys |

( 2 ) INFORMATION FOR SEQ ID NO:22:

( i ) SEQUENCE CHARACTERISTICS:
( A ) LENGTH: 236 amino acids
( B ) TYPE: amino acid
( D ) TOPOLOGY: linear ( x i ) SEQUENCE DESCRIPTION: SEQ ID NO:22:

| Met 1 | Ala | Gln | Ala | Gly 5 | Arg | Thr | Gly | Tyr | Asn 10 | Arg | Glu | Ile | Val 15 | Met |
| --- | --- | --- | --- | --- | --- | --- | --- | --- | --- | --- | --- | --- | --- | --- |
| Lys | Tyr | Ile | His 20 | Tyr | Lys | Leu | Ser | Gln 25 | Arg | Gly | Tyr | Glu | Trp 30 | Asp | Ala |
| Gly | Asp | Ala 35 | Asp | Ala | Ala | Pro | Leu 40 | Gly | Ala | Ala | Pro | Thr 45 | Pro | Gly | Ile |
| Phe | Ser 50 | Phe | Gln | Pro | Glu | Ser 55 | Asn | Pro | Met | Pro | Ala 60 | Val | His | Arg | Glu |
| Met 65 | Ala | Ala | Arg | Thr | Ser 70 | Pro | Leu | Arg | Pro | Leu 75 | Val | Ala | Thr | Ala | Gly 80 |
| Pro | Ala | Leu | Ser | Pro 85 | Val | Pro | Pro | Cys | Val 90 | His | Leu | Thr | Leu | Arg 95 | Arg |
| Ala | Gly | Asp | Asp 100 | Phe | Ser | Arg | Arg | Tyr 105 | Arg | Arg | Asp | Phe | Ala 110 | Glu | Met |
| Ser | Ser | Gln 115 | Leu | His | Leu | Thr | Pro 120 | Phe | Thr | Ala | Arg | Gly 125 | Arg | Phe | Ala |
| Thr | Val 130 | Val | Glu | Glu | Leu | Phe 135 | Arg | Asp | Gly | Val | Asn 140 | Trp | Gly | Arg | Ile |
| Val 145 | Ala | Phe | Phe | Glu | Phe 150 | Gly | Gly | Val | Met | Cys 155 | Val | Glu | Ser | Val | Asn 160 |
| Arg | Glu | Met | Ser | Pro 165 | Leu | Val | Asp | Asn | Ile 170 | Ala | Leu | Trp | Met | Thr 175 | Glu |
| Tyr | Leu | Asn | Arg 180 | His | Leu | His | Thr | Trp 185 | Ile | Gln | Asp | Asn | Gly 190 | Gly | Trp |
| Asp | Ala | Phe 195 | Val | Glu | Leu | Tyr | Gly 200 | Pro | Ser | Met | Arg | Pro 205 | Leu | Phe | Asp |
| Phe | Ser | Trp 210 | Leu | Ser | Leu | Lys 215 | Thr | Leu | Leu | Ser | Leu 220 | Ala | Leu | Val | Gly |
| Ala 225 | Cys | Ile | Thr | Leu | Gly 230 | Ala | Tyr | Leu | Gly | His 235 | Lys |

( 2 ) INFORMATION FOR SEQ ID NO:23:

(i) SEQUENCE CHARACTERISTICS:
  (A) LENGTH: 233 amino acids
  (B) TYPE: amino acid
  (D) TOPOLOGY: linear (xi) SEQUENCE DESCRIPTION: SEQ ID NO:23:

```
Met Ala His Pro Gly Arg Arg Gly Tyr Asp Asn Arg Glu Ile Val Leu
1               5                   10                  15

Lys Tyr Ile His Tyr Lys Leu Ser Gln Arg Gly Tyr Asp Trp Ala Ala
                20                  25                  30

Gly Glu Asp Arg Pro Pro Val Pro Pro Ala Pro Ala Pro Ala Ala Ala
            35                  40                  45

Pro Ala Ala Val Ala Ala Ala Gly Ala Ser Ser His His Arg Pro Glu
    50                  55                  60

Pro Pro Gly Ser Ala Ala Ala Ser Glu Val Pro Ala Glu Gly Leu
65                  70                  75                  80

Arg Pro Ala Pro Pro Gly Val His Leu Ala Leu Arg Gln Ala Gly Asp
                85                  90                  95

Glu Phe Ser Arg Arg Tyr Gln Arg Asp Phe Ala Gln Met Ser Gly Gln
                100                 105                 110

Leu His Leu Thr Pro Phe Thr Ala His Gly Arg Phe Val Ala Val Val
        115                 120                 125

Glu Glu Leu Phe Arg Asp Gly Val Asn Trp Gly Arg Ile Val Ala Phe
130                 135                 140

Phe Glu Phe Gly Gly Val Met Cys Val Glu Ser Val Asn Arg Glu Met
145                 150                 155                 160

Ser Pro Leu Val Asp Asn Ile Ala Thr Trp Met Thr Glu Tyr Leu Asn
                165                 170                 175

Arg His Leu His Asn Trp Ile Gln Asp Asn Gly Gly Trp Asp Ala Phe
            180                 185                 190

Val Glu Leu Tyr Gly Asn Ser Met Arg Pro Leu Phe Asp Phe Ser Trp
        195                 200                 205

Ile Ser Leu Lys Thr Ile Leu Ser Leu Val Leu Val Gly Ala Cys Ile
    210                 215                 220

Thr Leu Gly Ala Tyr Leu Gly His Lys
225                 230
```

(2) INFORMATION FOR SEQ ID NO:24:

(i) SEQUENCE CHARACTERISTICS:
  (A) LENGTH: 233 amino acids
  (B) TYPE: amino acid
  (D) TOPOLOGY: linear (xi) SEQUENCE DESCRIPTION: SEQ ID NO:24:

```
Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
                20                  25                  30

Asn Arg Thr Glu Ala Pro Glu Gly Thr Glu Ser Glu Met Glu Thr Pro
            35                  40                  45

Ser Ala Ile Asn Gly Asn Pro Ser Trp His Leu Ala Asp Ser Pro Ala
    50                  55                  60

Val Asn Gly Ala Thr Ala His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95
```

```
Phe  Glu  Leu  Arg  Tyr  Arg  Arg  Ala  Phe  Ser  Asp  Leu  Thr  Ser  Gln  Leu
               100                     105                     110

His  Ile  Thr  Pro  Gly  Thr  Ala  Tyr  Gln  Ser  Phe  Glu  Gln  Val  Val  Asn
               115                     120                     125

Glu  Leu  Phe  Arg  Asp  Gly  Val  Asn  Trp  Gly  Arg  Ile  Val  Ala  Phe  Phe
     130                     135                          140

Ser  Phe  Gly  Gly  Ala  Leu  Cys  Val  Glu  Ser  Val  Asp  Lys  Glu  Met  Gln
145                          150                     155                     160

Val  Leu  Val  Ser  Arg  Ile  Ala  Ala  Trp  Met  Ala  Thr  Tyr  Leu  Asn  Asp
               165                     170                     175

His  Leu  Glu  Pro  Trp  Ile  Gln  Glu  Asn  Gly  Gly  Trp  Asp  Thr  Phe  Val
               180                     185                     190

Glu  Leu  Tyr  Gly  Asn  Asn  Ala  Ala  Ala  Glu  Ser  Arg  Lys  Gly  Gln  Glu
          195                     200                     205

Arg  Phe  Asn  Arg  Trp  Phe  Leu  Thr  Gly  Met  Thr  Val  Ala  Gly  Val  Val
     210                     215                     220

Leu  Leu  Gly  Ser  Leu  Phe  Ser  Arg  Lys
225                     230
```

( 2 ) INFORMATION FOR SEQ ID NO:25:

( i ) SEQUENCE CHARACTERISTICS:
( A ) LENGTH: 192 amino acids
( B ) TYPE: amino acid
( D ) TOPOLOGY: linear ( x i ) SEQUENCE DESCRIPTION: SEQ ID NO:25:

```
Met  Asp  Gly  Ser  Gly  Glu  Gln  Pro  Arg  Gly  Gly  Gly  Pro  Thr  Ser  Ser
1                    5                    10                       15

Glu  Gln  Ile  Met  Lys  Thr  Gly  Ala  Leu  Leu  Leu  Gln  Gly  Phe  Ile  Gln
               20                     25                       30

Asp  Arg  Ala  Gly  Arg  Met  Gly  Gly  Glu  Ala  Pro  Glu  Leu  Ala  Leu  Asp
          35                     40                       45

Pro  Val  Pro  Gln  Asp  Ala  Ser  Thr  Lys  Lys  Leu  Ser  Glu  Cys  Leu  Lys
     50                     55                       60

Arg  Ile  Gly  Asp  Glu  Leu  Asp  Ser  Asn  Met  Glu  Leu  Gln  Arg  Met  Ile
65                    70                     75                       80

Ala  Ala  Val  Asp  Thr  Asp  Ser  Pro  Arg  Glu  Val  Phe  Phe  Arg  Val  Ala
               85                     90                       95

Ala  Asp  Met  Phe  Ser  Asp  Gly  Asn  Phe  Asn  Trp  Gly  Arg  Val  Val  Ala
               100                    105                      110

Leu  Phe  Tyr  Phe  Ala  Ser  Lys  Leu  Val  Leu  Lys  Ala  Leu  Cys  Thr  Lys
     115                    120                      125

Val  Pro  Glu  Leu  Ile  Arg  Thr  Ile  Met  Gly  Trp  Thr  Leu  Asp  Phe  Leu
     130                    135                      140

Arg  Glu  Arg  Leu  Leu  Gly  Trp  Ile  Gln  Asp  Gln  Gly  Gly  Trp  Asp  Gly
145                    150                    155                      160

Leu  Leu  Ser  Tyr  Phe  Gly  Thr  Pro  Thr  Trp  Gln  Thr  Val  Thr  Ile  Phe
                    165                    170                      175

Val  Ala  Gly  Val  Leu  Thr  Ala  Ser  Leu  Thr  Ile  Trp  Lys  Lys  Met  Gly
               180                    185                      190
```

( 2 ) INFORMATION FOR SEQ ID NO:26:

( i ) SEQUENCE CHARACTERISTICS:
( A ) LENGTH: 350 amino acids
( B ) TYPE: amino acid ( D ) TOPOLOGY: linear ( x i ) SEQUENCE DESCRIPTION: SEQ ID NO:26:

| Met | Phe | Gly | Leu | Lys | Arg | Asn | Ala | Val | Ile | Gly | Leu | Asn | Leu | Tyr | Cys |
|---|---|---|---|---|---|---|---|---|---|---|---|---|---|---|---|
| 1 | | | | 5 | | | | | 10 | | | | | 15 | |
| Gly | Gly | Ala | Gly | Leu | Gly | Ala | Gly | Ser | Gly | Gly | Ala | Thr | Arg | Pro | Gly |
| | | | 20 | | | | | 25 | | | | | 30 | | |
| Gly | Arg | Leu | Leu | Ala | Thr | Glu | Lys | Glu | Ala | Ser | Ala | Arg | Arg | Glu | Ile |
| | | 35 | | | | | 40 | | | | | 45 | | | |
| Gly | Gly | Gly | Glu | Ala | Gly | Ala | Val | Ile | Gly | Gly | Ser | Ala | Gly | Ala | Ser |
| | | | 50 | | | | 55 | | | | | 60 | | | |
| Pro | Pro | Ser | Thr | Leu | Thr | Pro | Asp | Ser | Arg | Arg | Val | Ala | Arg | Pro | Pro |
| 65 | | | | | 70 | | | | | 75 | | | | | 80 |
| Pro | Ile | Gly | Ala | Glu | Val | Pro | Asp | Val | Thr | Ala | Thr | Pro | Ala | Arg | Leu |
| | | | | 85 | | | | | 90 | | | | | 95 | |
| Leu | Phe | Phe | Ala | Pro | Thr | Arg | Arg | Ala | Ala | Pro | Leu | Glu | Glu | Met | Glu |
| | | | | 100 | | | | | 105 | | | | | 110 | |
| Ala | Pro | Ala | Ala | Asp | Ala | Ile | Met | Ser | Pro | Glu | Glu | Glu | Leu | Asp | Gly |
| | | | 115 | | | | 120 | | | | | 125 | | | |
| Tyr | Glu | Pro | Glu | Pro | Leu | Gly | Lys | Arg | Pro | Ala | Val | Leu | Pro | Leu | Leu |
| | 130 | | | | | 135 | | | | | 140 | | | | |
| Glu | Leu | Val | Gly | Glu | Ser | Gly | Asn | Asn | Thr | Ser | Thr | Asp | Gly | Ser | Leu |
| 145 | | | | | 150 | | | | | 155 | | | | | 160 |
| Pro | Ser | Thr | Pro | Pro | Pro | Ala | Glu | Glu | Glu | Glu | Asp | Glu | Leu | Tyr | Arg |
| | | | | 165 | | | | | 170 | | | | | 175 | |
| Gln | Ser | Leu | Glu | Ile | Ile | Ser | Arg | Tyr | Leu | Arg | Glu | Gln | Ala | Thr | Gly |
| | | | 180 | | | | | 185 | | | | | 190 | | |
| Ala | Lys | Asp | Thr | Lys | Pro | Met | Gly | Arg | Ser | Gly | Ala | Thr | Ser | Arg | Lys |
| | | 195 | | | | | 200 | | | | | 205 | | | |
| Ala | Leu | Glu | Thr | Leu | Arg | Arg | Val | Gly | Asp | Gly | Val | Gln | Arg | Asn | His |
| | 210 | | | | | 215 | | | | | 220 | | | | |
| Glu | Thr | Val | Phe | Gln | Gly | Met | Leu | Arg | Lys | Leu | Asp | Ile | Lys | Asn | Glu |
| 225 | | | | | 230 | | | | | 235 | | | | | 240 |
| Asp | Asp | Val | Lys | Ser | Leu | Ser | Arg | Val | Met | Ile | His | Val | Phe | Ser | Asp |
| | | | | 245 | | | | | 250 | | | | | 255 | |
| Gly | Val | Thr | Asn | Trp | Gly | Arg | Ile | Val | Thr | Leu | Ile | Ser | Phe | Gly | Ala |
| | | | 260 | | | | | 265 | | | | | 270 | | |
| Phe | Val | Ala | Lys | His | Leu | Lys | Thr | Ile | Asn | Gln | Glu | Ser | Cys | Ile | Glu |
| | | | 275 | | | | | 280 | | | | | 285 | | |
| Pro | Leu | Ala | Glu | Ser | Ile | Thr | Asp | Val | Leu | Val | Arg | Thr | Lys | Arg | Asp |
| | 290 | | | | | 295 | | | | | 300 | | | | |
| Trp | Leu | Val | Lys | Gln | Arg | Gly | Trp | Asp | Gly | Phe | Val | Glu | Phe | Phe | His |
| 305 | | | | | 310 | | | | | 315 | | | | | 320 |
| Val | Glu | Asp | Leu | Glu | Gly | Gly | Ile | Arg | Asn | Val | Leu | Leu | Ala | Phe | Ala |
| | | | | 325 | | | | | 330 | | | | | 335 | |
| Gly | Val | Ala | Gly | Val | Gly | Ala | Gly | Leu | Ala | Tyr | Leu | Ile | Arg | | |
| | | | 340 | | | | | 345 | | | | | 350 | | |

( 2 ) INFORMATION FOR SEQ ID NO:27:

( i ) SEQUENCE CHARACTERISTICS:
    ( A ) LENGTH: 179 amino acids
    ( B ) TYPE: amino acid
    ( D ) TOPOLOGY: linear ( x i ) SEQUENCE DESCRIPTION: SEQ ID NO:27:

```
Met  Glu  Gly  Glu  Glu  Leu  Ile  Tyr  His  Asn  Ile  Ile  Asn  Glu  Ile  Leu
1                   5                   10                       15

Val  Gly  Tyr  Ile  Lys  Tyr  Tyr  Met  Asn  Asp  Ile  Ser  Glu  His  Glu  Leu
               20                   25                       30

Ser  Pro  Tyr  Gln  Gln  Gln  Ile  Lys  Lys  Ile  Leu  Thr  Tyr  Tyr  Asp  Glu
               35                   40                   45

Cys  Leu  Asn  Lys  Gln  Val  Thr  Ile  Thr  Phe  Ser  Leu  Thr  Asn  Ala  Gln
     50                        55                   60

Glu  Ile  Lys  Thr  Gln  Phe  Thr  Gly  Val  Val  Thr  Glu  Leu  Phe  Lys  Asp
65                        70                   75                        80

Leu  Ile  Asn  Trp  Gly  Arg  Ile  Cys  Gly  Phe  Ile  Val  Phe  Ser  Ala  Arg
                    85                   90                             95

Met  Ala  Lys  Tyr  Cys  Lys  Asp  Ala  Asn  Asn  His  Leu  Glu  Ser  Thr  Val
               100                  105                      110

Ile  Thr  Thr  Ala  Tyr  Asn  Phe  Met  Lys  His  Asn  Leu  Leu  Pro  Trp  Met
          115                      120                  125

Ile  Ser  His  Gly  Gly  Gln  Glu  Glu  Phe  Leu  Ala  Phe  Ser  Leu  His  Ser
     130                      135                  140

Asp  Ile  Tyr  Ser  Val  Ile  Phe  Asn  Ile  Lys  Tyr  Phe  Leu  Ser  Lys  Phe
145                      150                  155                       160

Cys  Asn  His  Met  Phe  Leu  Arg  Ser  Cys  Val  Gln  Leu  Leu  Arg  Asn  Cys
               165                      170                       175

Asn  Leu  Ile
```

( 2 ) INFORMATION FOR SEQ ID NO:28:

( i ) SEQUENCE CHARACTERISTICS:
        ( A ) LENGTH: 191 amino acids
        ( B ) TYPE: amino acid
        ( D ) TOPOLOGY: linear ( x i ) SEQUENCE DESCRIPTION: SEQ ID NO:28:

```
Met  Ala  Tyr  Ser  Thr  Arg  Glu  Ile  Leu  Leu  Ala  Leu  Cys  Ile  Arg  Asp
1                   5                   10                       15

Ser  Arg  Val  His  Gly  Asn  Gly  Thr  Leu  His  Pro  Val  Leu  Glu  Leu  Ala
               20                   25                       30

Ala  Arg  Glu  Thr  Pro  Leu  Arg  Leu  Ser  Pro  Glu  Asp  Thr  Val  Val  Leu
               35                   40                   45

Arg  Tyr  His  Val  Leu  Leu  Glu  Glu  Ile  Ile  Glu  Arg  Asn  Ser  Glu  Thr
     50                        55                   60

Phe  Thr  Glu  Thr  Trp  Asn  Arg  Phe  Ile  Thr  His  Thr  Glu  His  Val  Asp
65                        70                   75                        80

Leu  Asp  Phe  Asn  Ser  Val  Phe  Leu  Glu  Ile  Phe  His  Arg  Gly  Asp  Pro
                    85                   90                             95

Ser  Leu  Gly  Arg  Ala  Leu  Ala  Trp  Met  Ala  Trp  Cys  Met  His  Ala  Cys
               100                  105                      110

Arg  Thr  Leu  Cys  Cys  Asn  Gln  Ser  Thr  Pro  Tyr  Tyr  Val  Val  Asp  Leu
          115                      120                  125

Ser  Val  Arg  Gly  Met  Leu  Glu  Ala  Ser  Glu  Gly  Leu  Asp  Gly  Trp  Ile
     130                      135                  140

His  Gln  Gln  Gly  Gly  Trp  Ser  Thr  Leu  Ile  Glu  Asp  Asn  Ile  Pro  Gly
145                      150                  155                       160

Ser  Arg  Arg  Phe  Ser  Trp  Thr  Leu  Phe  Leu  Ala  Gly  Leu  Thr  Leu  Ser
               165                      170                       175

Leu  Leu  Val  Ile  Cys  Ser  Tyr  Leu  Phe  Ile  Ser  Arg  Gly  Arg  His
               180                      185                       190
```

(2) INFORMATION FOR SEQ ID NO:29:

(i) SEQUENCE CHARACTERISTICS:
        (A) LENGTH: 236 amino acids
        (B) TYPE: amino acid
        (D) TOPOLOGY: linear (xi) SEQUENCE DESCRIPTION: SEQ ID NO:29:

```
Met Ala Xaa Xaa Gly Xaa Xaa Xaa Xaa Xaa Asn Arg Glu Ile Val Xaa
 1               5                   10                  15
Xaa Xaa Xaa Xaa Tyr Lys Leu Ser Gln Arg Gly Tyr Xaa Trp Xaa Xaa
             20                  25                  30
Gly Xaa Xaa Xaa Xaa Xaa Xaa Xaa Xaa Xaa Ala Pro Xaa Pro Gly Xaa
         35                  40                  45
Xaa Xaa Xaa Xaa Xaa Xaa Xaa Xaa Xaa Xaa Xaa Xaa Xaa Xaa Xaa Xaa
     50                  55                  60
Xaa Xaa Xaa Xaa Xaa Xaa Xaa Leu Xaa Xaa Xaa Xaa Xaa Xaa Xaa Xaa
 65                  70                  75                  80
Xaa Xaa Leu Xaa Pro Xaa Xaa Xaa Xaa Xaa Xaa Leu Xaa Leu Arg Arg
             85                  90                  95
Ala Gly Asp Xaa Phe Xaa Arg Arg Tyr Xaa Arg Xaa Phe Xaa Xaa Met
            100                 105                 110
Xaa Xaa Gln Leu His Leu Thr Pro Xaa Thr Ala Xaa Xaa Xaa Phe Xaa
        115                 120                 125
Xaa Val Val Xaa Glu Leu Phe Arg Asp Gly Val Asn Trp Gly Arg Ile
    130                 135                 140
Val Ala Phe Phe Xaa Phe Gly Gly Xaa Met Cys Val Xaa Ser Val Xaa
145                 150                 155                 160
Xaa Glu Met Xaa Pro Leu Val Xaa Xaa Ile Ala Xaa Trp Met Thr Xaa
                165                 170                 175
Tyr Leu Asn Arg His Leu Xaa Xaa Trp Ile Gln Asp Asn Gly Gly Trp
            180                 185                 190
Asp Xaa Phe Val Glu Leu Tyr Gly Xaa Ser Xaa Arg Xaa Xaa Xaa Asp
        195                 200                 205
Phe Ser Trp Xaa Xaa Xaa Xaa Xaa Xaa Leu Xaa Leu Xaa Xaa Val Xaa
    210                 215                 220
Ala Cys Xaa Thr Leu Gly Ala Tyr Leu Gly Xaa Lys
225                 230                 235
```